United States Patent
Niemiec et al.

(10) Patent No.: US 10,143,500 B2
(45) Date of Patent: Dec. 4, 2018

(54) DEVICES AND METHODS FOR CORRECTING VERTEBRAL MISALIGNMENT

(71) Applicant: GLOBUS MEDICAL, INC., Audubon, PA (US)

(72) Inventors: Marcin Niemiec, Norristown, PA (US); Nick Padovani, Wynnewood, PA (US); Matthew Hansell, Schwenksville, PA (US); Duncan Sibson, Malvern, PA (US); Adam Friedrich, Cinnaminson, NJ (US); Khiem Pham, Chalfont, PA (US); Noah Hansell, King of Prussia, PA (US); Ben Silber, Flemington, NJ (US); Andrew Iott, Newtown Square, PA (US)

(73) Assignee: Globus Medical, Inc., Audubon, PA (US)

(*) Notice: Subject to any disclaimer, the term of this patent is extended or adjusted under 35 U.S.C. 154(b) by 136 days.

(21) Appl. No.: 15/410,935

(22) Filed: Jan. 20, 2017

(65) Prior Publication Data

US 2017/0128108 A1 May 11, 2017

Related U.S. Application Data

(63) Continuation of application No. 13/767,468, filed on Feb. 14, 2013, now Pat. No. 9,585,765.

(51) Int. Cl.
*A61B 17/56* (2006.01)
*A61B 17/70* (2006.01)
(Continued)

(52) U.S. Cl.
CPC ...... *A61B 17/7059* (2013.01); *A61B 17/7097* (2013.01); *A61B 17/86* (2013.01);
(Continued)

(58) Field of Classification Search
CPC ...... A61F 2/442; A61F 2/4611; A61F 2/4455; A61F 2/447; A61F 2/44
See application file for complete search history.

(56) References Cited

U.S. PATENT DOCUMENTS

| 5,163,949 A | 11/1992 | Bonutti |
| 5,163,960 A | 11/1992 | Bonutti |

(Continued)

FOREIGN PATENT DOCUMENTS

| FR | 2727003 A1 | 5/1996 |
| WO | 1997023175 A1 | 7/1997 |

(Continued)

OTHER PUBLICATIONS

U.S. Appl. No. 60/777,663, filed Jun. 27, 2006, Messerli.
(Continued)

*Primary Examiner* — Lynnsy Summitt

(57) ABSTRACT

Embodiments of devices and methods of correcting vertebral misalignment, including, e.g., spondylolisthesis, are disclosed. In one embodiment, a vertebral implant may include an assembly configured to be secured to a first vertebral body, wherein the assembly includes a frame made of a first material and at least one end plate made of a second material different than the first material; a reducing plate configured to be slidably received over the central portion, wherein the reducing plate is configured to be secured to a second vertebral body; and an actuator configured to move the reducing plate relative to the frame.

20 Claims, 21 Drawing Sheets

(51) Int. Cl.
*A61F 2/44* (2006.01)
*A61F 2/46* (2006.01)
*A61B 17/86* (2006.01)
*A61F 2/30* (2006.01)

(52) U.S. Cl.
CPC .......... *A61F 2/30767* (2013.01); *A61F 2/447* (2013.01); *A61F 2/4455* (2013.01); *A61F 2/4611* (2013.01); *A61B 2017/564* (2013.01); *A61F 2/441* (2013.01); *A61F 2002/305* (2013.01); *A61F 2002/3008* (2013.01); *A61F 2002/308* (2013.01); *A61F 2002/30131* (2013.01); *A61F 2002/30242* (2013.01); *A61F 2002/30331* (2013.01); *A61F 2002/30372* (2013.01); *A61F 2002/30448* (2013.01); *A61F 2002/30451* (2013.01); *A61F 2002/30482* (2013.01); *A61F 2002/30484* (2013.01); *A61F 2002/30489* (2013.01); *A61F 2002/30507* (2013.01); *A61F 2002/30509* (2013.01); *A61F 2002/30537* (2013.01); *A61F 2002/30604* (2013.01); *A61F 2002/30677* (2013.01); *A61F 2002/30733* (2013.01); *A61F 2002/30772* (2013.01); *A61F 2002/30787* (2013.01); *A61F 2002/30904* (2013.01); *A61F 2002/4475* (2013.01); *A61F 2310/0097* (2013.01); *A61F 2310/00293* (2013.01)

(56) References Cited

U.S. PATENT DOCUMENTS

| | | |
|---|---|---|
| 5,197,971 A | 3/1993 | Bonutti |
| 5,269,785 A | 12/1993 | Bonutti |
| 5,295,994 A | 3/1994 | Bonutti |
| 5,329,846 A | 7/1994 | Bonutti |
| 5,331,975 A | 7/1994 | Bonutti |
| 5,345,927 A | 9/1994 | Bonutti |
| 5,397,364 A | 3/1995 | Kozak et al. |
| 5,403,317 A | 4/1995 | Bonutti |
| 5,403,348 A | 4/1995 | Bonutti |
| 5,441,538 A | 8/1995 | Bonutti |
| 5,454,365 A | 10/1995 | Bonutti |
| 5,458,641 A | 10/1995 | Jiminez |
| 5,464,426 A | 11/1995 | Bonutti |
| 5,496,348 A | 3/1996 | Bonutti |
| 5,514,153 A | 5/1996 | Bonutti |
| 5,522,846 A | 6/1996 | Bonutti |
| 5,527,343 A | 6/1996 | Bonutti |
| 5,534,012 A | 7/1996 | Bonutti |
| 5,545,222 A | 8/1996 | Bonutti |
| 5,549,612 A | 8/1996 | Yapp et al. |
| 5,549,630 A | 8/1996 | Bonutti |
| 5,549,631 A | 8/1996 | Bonutti |
| 5,569,305 A | 10/1996 | Bonutti |
| 5,577,517 A | 11/1996 | Bonutti |
| 5,584,862 A | 12/1996 | Bonutti |
| 5,593,425 A | 1/1997 | Bonutti |
| 5,624,462 A | 4/1997 | Bonutti |
| 5,662,710 A | 9/1997 | Bonutti |
| 5,667,520 A | 9/1997 | Bonutti |
| 5,685,826 A | 11/1997 | Bonutti |
| 5,694,951 A | 12/1997 | Bonutti |
| 5,707,390 A | 1/1998 | Bonutti |
| 5,716,325 A | 2/1998 | Bonutti |
| 5,733,306 A | 3/1998 | Bonutti |
| 5,735,875 A | 4/1998 | Bonutti |
| 5,827,318 A | 10/1998 | Bonutti |
| 5,845,645 A | 12/1998 | Bonutti |
| 5,860,997 A | 1/1999 | Bonutti |
| 5,861,041 A | 1/1999 | Tienboon |
| 5,888,196 A | 3/1999 | Bonutti |
| 5,888,219 A | 3/1999 | Bonutti |
| 5,888,223 A | 3/1999 | Bray, Jr. |
| 5,928,267 A | 7/1999 | Bonutti |
| 5,935,131 A | 8/1999 | Bonutti |
| 5,941,900 A | 8/1999 | Bonutti |
| 5,954,739 A | 9/1999 | Bonutti |
| 6,010,525 A | 1/2000 | Bonutti |
| 6,017,305 A | 1/2000 | Bonutti |
| 6,042,596 A | 3/2000 | Bonutti |
| 6,059,817 A | 5/2000 | Bonutti |
| 6,066,175 A | 5/2000 | Henderson et al. |
| 6,077,292 A | 6/2000 | Bonutti |
| 6,086,593 A | 7/2000 | Bonutti |
| 6,099,531 A | 8/2000 | Bonutti |
| 6,102,928 A | 8/2000 | Bonutti |
| 6,132,472 A | 10/2000 | Bonutti |
| RE36,974 E | 11/2000 | Bonutti |
| 6,156,037 A | 12/2000 | LeHuec et al. |
| 6,159,234 A | 12/2000 | Bonutti |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,200,347 B1 | 3/2001 | Anderson et al. |
| 6,203,565 B1 | 3/2001 | Bonutti |
| 6,206,922 B1 | 3/2001 | Zdeblick et al. |
| 6,217,617 B1 | 4/2001 | Bonutti |
| 6,231,592 B1 | 5/2001 | Bonutti |
| 6,231,610 B1 | 5/2001 | Geisler |
| 6,258,089 B1 | 7/2001 | Campbell et al. |
| 6,277,136 B1 | 8/2001 | Bonutti |
| 6,287,325 B1 | 9/2001 | Bonutti |
| 6,358,266 B1 | 3/2002 | Bonutti |
| 6,361,565 B1 | 3/2002 | Bonutti |
| 6,368,343 B1 | 4/2002 | Bonutti |
| 6,383,186 B1 | 5/2002 | Michelson |
| 6,432,106 B1 | 8/2002 | Fraser |
| 6,447,516 B1 | 9/2002 | Bonutti |
| 6,451,042 B1 | 9/2002 | Bonutti |
| 6,464,713 B2 | 10/2002 | Bonutti |
| 6,468,289 B1 | 10/2002 | Bonutti |
| 6,468,293 B2 | 10/2002 | Bonutti |
| 6,475,230 B1 | 11/2002 | Bonutti |
| 6,482,233 B1 | 11/2002 | Aebi |
| 6,500,195 B2 | 12/2002 | Bonutti |
| 6,503,267 B2 | 1/2003 | Bonutti |
| 6,503,277 B2 | 1/2003 | Bonutti |
| 6,540,785 B1 | 4/2003 | Gill et al. |
| 6,543,455 B2 | 4/2003 | Bonutti |
| 6,558,423 B1 | 5/2003 | Michelson |
| 6,558,424 B2 | 5/2003 | Thalgott |
| 6,569,187 B1 | 5/2003 | Bonutti |
| 6,575,982 B1 | 6/2003 | Bonutti |
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,620,181 B1 | 9/2003 | Bonutti |
| 6,630,000 B1 | 10/2003 | Bonutti |
| 6,635,073 B2 | 10/2003 | Bonutti |
| 6,638,309 B2 | 10/2003 | Bonutti |
| 6,652,532 B2 | 11/2003 | Bonutti |
| 6,666,889 B1 | 12/2003 | Commarmond |
| 6,702,821 B2 | 3/2004 | Bonutti |
| 6,702,856 B2 | 3/2004 | Bonutti |
| 6,719,803 B2 | 4/2004 | Bonutti |
| 6,736,853 B2 | 5/2004 | Bonutti |
| 6,740,118 B2 | 5/2004 | Eisermann et al. |
| 6,770,078 B2 | 8/2004 | Bonutti |
| 6,776,938 B2 | 8/2004 | Bonutti |
| 6,827,740 B1 | 12/2004 | Michelson |
| 6,835,198 B2 | 12/2004 | Bonutti |
| 6,860,885 B2 | 3/2005 | Bonutti |
| 6,860,904 B2 | 3/2005 | Bonutti |
| 6,899,735 B2 | 5/2005 | Coates et al. |
| 6,905,517 B2 | 6/2005 | Bonutti |
| 6,908,466 B1 | 6/2005 | Bonutti |
| 6,932,835 B2 | 8/2005 | Bonutti |
| 6,972,019 B2 | 12/2005 | Michelson |
| 6,989,029 B2 | 1/2006 | Bonutti |
| 6,990,982 B1 | 1/2006 | Bonutti |

(56) References Cited

U.S. PATENT DOCUMENTS

| | | |
|---|---|---|
| 7,001,432 B2 | 2/2006 | Keller et al. |
| 7,025,787 B2 | 4/2006 | Bryan et al. |
| 7,048,755 B2 | 5/2006 | Bonutti |
| 7,070,557 B2 | 7/2006 | Bonutti |
| 7,087,073 B2 | 8/2006 | Bonutti |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti |
| 7,134,437 B2 | 11/2006 | Bonutti |
| 7,137,997 B2 | 11/2006 | Paul |
| 7,147,652 B2 | 12/2006 | Bonutti |
| 7,147,665 B1 | 12/2006 | Bryan et al. |
| 7,153,325 B2 | 12/2006 | Kim et al. |
| 7,172,627 B2 | 2/2007 | Fiere et al. |
| 7,208,013 B1 | 4/2007 | Bonutti |
| 7,217,273 B2 | 5/2007 | Bonutti |
| 7,217,290 B2 | 5/2007 | Bonutti |
| 7,232,464 B2 | 6/2007 | Mathieu et al. |
| 7,276,082 B2 | 10/2007 | Zdeblick et al. |
| 7,309,357 B2 | 12/2007 | Kim |
| 7,311,719 B2 | 12/2007 | Bonutti |
| 7,320,708 B1 | 1/2008 | Bernstein |
| 7,329,263 B2 | 2/2008 | Bonutti |
| 7,429,266 B2 | 9/2008 | Bonutti |
| 7,462,200 B2 | 12/2008 | Bonutti |
| 7,481,831 B2 | 1/2009 | Bonutti |
| 7,510,557 B1 | 3/2009 | Bonutti |
| 7,615,054 B1 | 11/2009 | Bonutti |
| 7,618,456 B2 | 11/2009 | Mathieu et al. |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,771,475 B2 | 8/2010 | Michelson |
| 7,780,670 B2 | 8/2010 | Bonutti |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,846,207 B2 | 12/2010 | Lechmann et al. |
| 7,854,750 B2 | 12/2010 | Bonutti |
| 7,862,616 B2 | 1/2011 | Lechmann et al. |
| 7,875,076 B2 | 1/2011 | Mathieu et al. |
| 7,879,072 B2 | 2/2011 | Bonutti |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,942,903 B2 * | 5/2011 | Moskowitz ......... A61B 17/0642 606/251 |
| 7,959,635 B1 | 6/2011 | Bonutti |
| 8,100,976 B2 | 1/2012 | Bray et al. |
| 8,128,669 B2 | 3/2012 | Bonutti |
| 8,133,229 B1 | 3/2012 | Bonutti |
| 8,162,977 B2 | 4/2012 | Bonutti |
| 8,262,666 B2 * | 9/2012 | Baynham ............ A61F 2/4455 606/86 A |
| 8,343,222 B2 | 1/2013 | Cope |
| 8,425,522 B2 | 4/2013 | Bonutti |
| 8,486,066 B2 | 7/2013 | Bonutti |
| 8,556,975 B2 * | 10/2013 | Ciupik .................. A61F 2/4455 606/105 |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 9,149,368 B1 * | 10/2015 | Jensen .................... A61F 2/447 |
| 9,987,142 B2 * | 6/2018 | McConnell .......... A61F 2/4455 |
| 2001/0023371 A1 | 9/2001 | Bonutti |
| 2002/0010511 A1 | 1/2002 | Michelson |
| 2002/0016595 A1 | 2/2002 | Michelson |
| 2002/0029055 A1 | 3/2002 | Bonutti |
| 2002/0040246 A1 | 4/2002 | Bonutti |
| 2002/0095160 A1 | 7/2002 | Bonutti |
| 2003/0009147 A1 | 1/2003 | Bonutti |
| 2003/0023260 A1 | 1/2003 | Bonutti |
| 2003/0045939 A1 | 3/2003 | Casutt |
| 2003/0105528 A1 | 6/2003 | Shimp et al. |
| 2003/0125739 A1 | 7/2003 | Bagga et al. |
| 2003/0167091 A1 | 9/2003 | Scharf |
| 2004/0010287 A1 | 1/2004 | Bonutti |
| 2004/0078078 A1 | 4/2004 | Shepard |
| 2004/0097794 A1 | 5/2004 | Bonutti |
| 2004/0098016 A1 | 5/2004 | Bonutti |
| 2004/0138689 A1 | 7/2004 | Bonutti |
| 2004/0138690 A1 | 7/2004 | Bonutti |
| 2004/0143270 A1 | 7/2004 | Zucherman et al. |
| 2004/0143285 A1 | 7/2004 | Bonutti |
| 2004/0143332 A1 | 7/2004 | Krueger et al. |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0230223 A1 | 11/2004 | Bonutti |
| 2005/0055098 A1 | 3/2005 | Zdeblick et al. |
| 2005/0065607 A1 | 3/2005 | Gross |
| 2005/0101960 A1 | 5/2005 | Fiere |
| 2005/0149192 A1 | 7/2005 | Zuchermann et al. |
| 2005/0149193 A1 | 7/2005 | Zuchermann et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0216059 A1 | 9/2005 | Bonutti |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2005/0267534 A1 | 12/2005 | Bonutti |
| 2006/0085071 A1 | 4/2006 | Lechmann et al. |
| 2006/0129240 A1 | 6/2006 | Lessar et al. |
| 2006/0167495 A1 | 7/2006 | Bonutti |
| 2006/0217809 A1 | 9/2006 | Albert et al. |
| 2006/0235470 A1 | 10/2006 | Bonutti |
| 2006/0265009 A1 | 11/2006 | Bonutti |
| 2007/0088441 A1 | 4/2007 | Duggal et al. |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0208378 A1 | 9/2007 | Bonutti |
| 2007/0225806 A1 | 9/2007 | Squires et al. |
| 2007/0225812 A1 | 9/2007 | Gill |
| 2007/0233253 A1 | 10/2007 | Bray et al. |
| 2007/0250167 A1 | 10/2007 | Bray et al. |
| 2007/0270961 A1 | 11/2007 | Ferguson |
| 2008/0033440 A1 * | 2/2008 | Moskowitz ......... A61B 17/0642 606/251 |
| 2008/0039873 A1 | 2/2008 | Bonutti |
| 2008/0047567 A1 | 2/2008 | Bonutti |
| 2008/0051890 A1 | 2/2008 | Waugh et al. |
| 2008/0051907 A1 | 2/2008 | Marik |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0133013 A1 | 6/2008 | Duggal et al. |
| 2008/0140011 A1 | 6/2008 | Bonutti |
| 2008/0140117 A1 | 6/2008 | Bonutti |
| 2009/0076608 A1 | 3/2009 | Gordon et al. |

(56) References Cited

U.S. PATENT DOCUMENTS

| | | |
|---|---|---|
| 2009/0192616 A1 | 7/2009 | Zielinski |
| 2009/0210062 A1 | 8/2009 | Thalgott et al. |
| 2010/0204737 A1 | 8/2010 | Bae et al. |
| 2011/0144755 A1* | 6/2011 | Baynham ................ A61F 2/447 623/17.16 |
| 2012/0010623 A1 | 1/2012 | Bonutti |
| 2012/0215226 A1 | 8/2012 | Bonutti |
| 2012/0215233 A1 | 8/2012 | Bonutti |
| 2012/0221017 A1 | 8/2012 | Bonutti |
| 2013/0226185 A1 | 8/2013 | Bonutti |
| 2013/0237989 A1 | 9/2013 | Bonutti |
| 2013/0289729 A1 | 10/2013 | Bonutti |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0228963 A1 | 8/2014 | Bonutti |
| 2014/0257380 A1 | 9/2014 | Bonutti |
| 2014/0309560 A1 | 10/2014 | Bonutti |
| 2014/0343573 A1 | 11/2014 | Bonutti |

FOREIGN PATENT DOCUMENTS

| | | |
|---|---|---|
| WO | 199848739 A1 | 11/1998 |
| WO | 1999063914 A1 | 12/1999 |
| WO | 2004/037067 A2 | 5/2004 |
| WO | 2005007040 A1 | 1/2005 |
| WO | 2007098288 A2 | 8/2007 |
| WO | 2008014258 A2 | 1/2008 |
| WO | 2010/028095 A1 | 3/2010 |

OTHER PUBLICATIONS

U.S. Appl. No. 60/777,732, filed Feb. 27, 2006, Messerli et al.

U.S. Appl. No. 60/838,229, filed Aug. 16, 2006, Hunziker et al.

Guidance Document: Intervertebral Body Fusion Device, U.S. Dept. of Health and Human Services, Food and Drug Administration (Jun. 12, 2007).

M. Spruit et al., The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner

DEVICES AND METHODS FOR CORRECTING VERTEBRAL MISALIGNMENT

CROSS-REFERENCE TO RELATED APPLICATIONS

This application is a continuation application of U.S. patent application Ser. No. 13/767,468 filed on Feb. 14, 2013 (published as U.S. Patent Publication No. 2014/0228958), the disclosure of which is incorporated herein by reference in its entirety.

FIELD OF THE INVENTION

Embodiments of the present disclosure relate generally to correcting misalignment of vertebral bodies comprising the spinal column. More particularly, embodiments of the present disclosure relate to stabilizing dislocated vertebral bodies to, among other things, correct spondylolisthesis and other spinal column injuries or deformities.

BACKGROUND

Spondylolisthesis is a medical condition in which one vertebral body slips (e.g., anteriorly) in relation to an adjacent vertebral body, usually in the lumbar region of the spine. This condition can cause symptoms that include pain in the lower back, thighs, and/or legs, muscle spasms, weakness, and/or tight hamstring muscles. In some cases, however, the presence of spondylolisthesis can be identified only by radiographic imaging (e.g., X-ray).

One solution for correcting spondylolisthesis and other similar conditions of vertebral dislocation may include reconstructive surgery and fusion of the affected vertebral body to an adjacent vertebral body. Vertebral fusion is generally accomplished by removing the native disc and then fixing an apparatus to and between the misaligned vertebrae. In addition to the stabilization and correction of spondylolisthesis, embodiments of the present disclosure may facilitate correction or treatment of other spinal conditions, including, but not limited to, stabilization of fractures, correction of spinal deformities (e.g. scoliosis and/or kyphosis), stabilization and correction of degenerative spinal lesions and narrow spinal canal, reconstruction after tumor resection, and secondary spinal surgery.

SUMMARY OF THE INVENTION

Embodiments of the present disclosure relate to, among other things, correction of spondylolisthesis by movement of the vertebrae into better alignment while maintaining stabilization of the vertebrae in the new position. Further, embodiments of the present disclosure may be used to move one or more dislocated (e.g., slipped) vertebral bodies into a post-surgical position and keep the vertebrae in the post-surgical position during, e.g., ossification. Each of the embodiments disclosed herein may include one or more of the features described in connection with any of the other disclosed embodiments.

In one embodiment, a vertebral implant may include an assembly configured to be secured to a first vertebral body, wherein the assembly includes a frame made of a first material and at least one end plate made of a second material different than the first material; a reducing plate configured to be slidably received over the central portion, wherein the reducing plate is configured to be secured to a second vertebral body; and an actuator configured to move the reducing plate relative to the frame.

In another embodiment, a vertebral implant may include a frame assembly include a left lateral portion, a central portion, and a right lateral portion, wherein the left and right lateral portions define enlarged heads configured to receive fasteners therein for securing the frame assembly to a first vertebral body, and wherein the central portion defines a lumen therethrough; a reducing member configured to be slidably received over the central portion, wherein the reducing member includes an anterior portion and a plurality of plates extending posteriorly therefrom, wherein the plurality of plates define a channel therebetween, wherein the channel is configured to receive a portion of the central portion; and an actuator configured to control a position of the reducing member relative to the frame assembly.

In a further embodiment, a method of correcting vertebral misalignment may include positioning an implant within a space between two adjacent vertebral bodies, wherein the implant may include a frame assembly include a left lateral portion, a central portion, and a right lateral portion, wherein the left and right lateral portions define enlarged heads configured to receive fasteners therein for securing the frame assembly to a first vertebral body, and wherein the central portion defines a lumen therethrough; a reducing member configured to be slidably received over the central portion, wherein the reducing member includes an anterior portion and a plurality of plates extending posteriorly therefrom, wherein the plurality of plates define a channel therebetween, wherein the channel is configured to receive a portion of the central portion; and an actuator configured to control a position of the reducing member relative to the frame assembly. The method may further include securing the frame assembly to a first vertebral body of the two adjacent vertebral bodies; securing the reducing member to a second vertebral body of the two adjacent vertebral bodies, wherein the second vertebral body is disposed superiorly of the first vertebral body; rotating the actuator to move the second vertebral body relative to the first vertebral body; and securing the reducing member relative to the frame assembly.

In yet another embodiment, a method of correcting vertebral misalignment may include accessing adjacent vertebral bodies via an anterior-only approach; removing a native disc from in between the adjacent vertebral bodies to form an interbody disc space; roughening one or more surfaces of one or both of the adjacent vertebral bodies; positioning an implantable assembly within the interbody disc space. The implantable assembly may include a frame member having a substantially cylindrical central portion, wherein the frame member is configured to be secured to a first vertebral body of the adjacent vertebral bodies by a first fastener; a reducing member movably secured to the frame member, wherein the reducing member is configured to be slidably received over the cylindrical central portion, and wherein the reducing member is configured to be secured to a second vertebral body of the adjacent vertebral bodies by a second fastener; and an actuator for controlling a position of the reducing member relative to the frame member. The method may also include adjusting a position of one of the adjacent vertebral bodies relative to the other of the adjacent vertebral bodies.

In a further embodiment, a vertebral implant may include a head portion including a first counterbore, a second counterbore, a third counterbore, and a fourth counterbore; a plurality of planar longitudinal members extending away from the head portion, wherein the plurality of planar longitudinal members are spaced from one another to define a channel therebetween; and a plurality of endplates configured to be disposed on each of the plurality of planar longitudinal members.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Figure 1A:
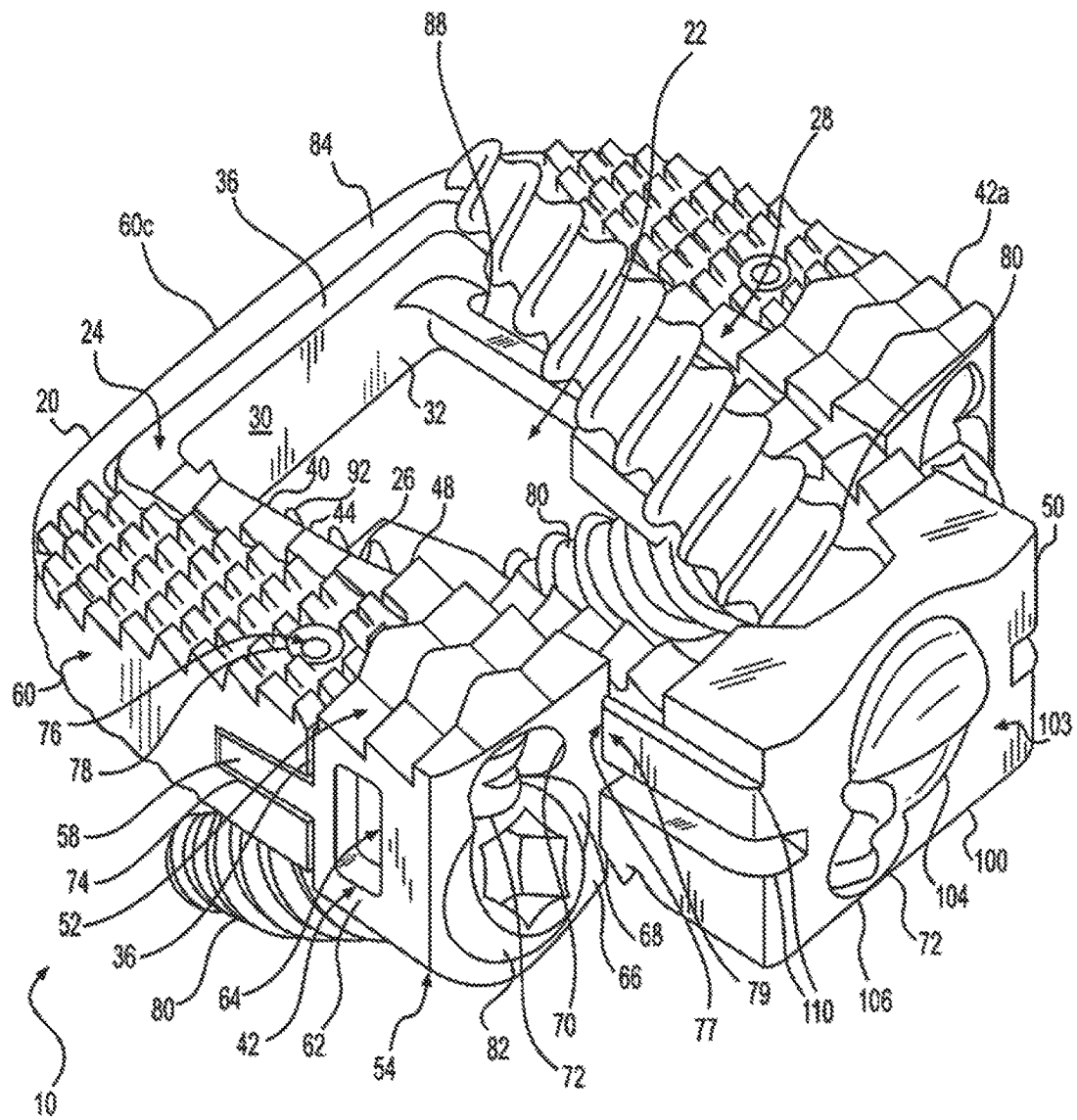
FIG. 1A depicts an isometric view of an apparatus for correcting vertebral misalignment in a first configuration, in accordance with an embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

It is understood that the exemplary devices and methods discussed below are described in connection with vertebral bodies, such as, e.g., the lumbar and sacral vertebral bodies. However, unless specifically noted, the disclosed embodiments are not limited to use in connection with vertebral bodies, or any particular vertebral bodies. Instead, the disclosed embodiments may have applicability in various parts of the body where it is desired to correct misalignment between adjacent structures. Moreover, the disclosed embodiments may be used in various procedures where the benefits of the described devices and methods are desired.

Exemplary Embodiments

Turning now to FIGS. 1A-1D, there is depicted an exemplary embodiment of an intervertebral implant assembly 10, in accordance with an embodiment of the present disclosure. As alluded to above, the implant assembly 10 may be used for, among other things, correcting misalignment of adjacent vertebral bodies, which may be commonly associated with, e.g., spondylolisthesis. The implant assembly 10 may include an outer member 20 and an inner member 50.

The outer member 20 may be configured to define a frame having a substantially U-shaped configuration. The U-shaped configuration may define a cavity/opening 22 therein. As discussed in greater detail below, the outer member 20 may be configured to at least partially receive at least a portion of the inner member 50 within cavity 22. The outer member 20 may include a first component 24, which may be a frame or frame-like member. First component 24 may be configured to provide structural rigidity to outer member 20.

In one embodiment, component 24 may include a substantially U-shaped configuration that defines cavity 22. As shown in FIG. 1A, component 24 may include a first leg 26, a second leg 28, and a connecting leg 30. Connecting leg 30 may define the base of the U-shaped configuration, with legs 26, 28 extending anteriorly therefrom. Connecting leg 30 may include substantially planar anterior 32 and posterior 34 (shown in FIG. 1B) surfaces. Similarly, connecting leg 30 may include substantially planar superior 36 and inferior 38 (shown in FIG. 1D) surfaces. In addition, some embodiments of superior and inferior surfaces 36, 38 may include a slant or taper extending away from the anterior surface 32 and narrowing toward opening/cavity 22. That is, in some embodiments, portions of assembly 10 may include a tapering configuration. In such embodiments, therefore, a width of posterior surface 34 may be smaller than the width of anterior surface 32. In other embodiments, however, the width of posterior surface 34 may be larger than the width of anterior surface 32. In further embodiments, a width of the anterior surface 32 may be substantially similar to a width of the posterior surface 34.

As noted above, first and second legs 26, 28 extend anteriorly away from connecting leg 30. It is contemplated that legs 26, 28 may be substantially similar to one another. Indeed, in one embodiment, legs 26, 28 may be effectively mirror images of each other. Thus, for the purposes of efficiency, only first leg 26 will be described herein. However, those of ordinary skill will understand that leg 28 may include some or all of the features of first leg 26. In addition, legs 26 and 28 do not necessarily have to be identical to one another. In fact, legs 26 and 28 may include differing configurations (not shown).

First leg 26 may include an extension portion 40 and a head portion 42. Extension portion 40 may be integrally formed with connecting leg 30 and extending anteriorly therefrom. In some embodiments, however, extension portion 40 may be fixedly secured to connecting leg 30 by any suitable means known in the art. For example, extension portion 40 may be welded to connecting leg 30. Extension portion 40 may include a substantially trapezoidal configuration. In other words, a transverse cross-sectional dimension may gradually increase along the length of extension portion 40. Extension portion 40 may include a superior surface 44 and an inferior surface 46. As discussed in greater detail below, both the superior 44 and inferior 46 surfaces may include geometrical features configured to promote gripping of tissue and/or bone surfaces. For example, the geometrical features may include pyramidal extensions 48 rising away from the respective superior 44 and inferior 46 surfaces. In another embodiment, the surfaces 44, 46 may include peaks, valleys, barbs, tines, a roughened surface, or any configuration suitable for promoting gripping of appropriate tissue and/or bone surfaces.

An anterior end of extension portion 40 may be integrally formed with head portion 42. In some embodiments, however, head portion 42 may be fixedly secured to extension portion 40 by, e.g., welding. Head portion 42 may include a height larger than a height of connecting leg 30. With particular reference to FIG. 1A, head portion 42 may be configured to extend laterally away from extension portion 40 in the direction away from cavity 22. Furthermore, like superior 44 and inferior 46 surfaces of extension portion 40, the superior 52 and inferior 54 surfaces of head portion 42 may include geometric features for aiding in the gripping of tissue or bone surfaces. In addition, the superior 52 and inferior 54 surfaces may include a stepped configuration, which allows head portion 42 to gradually increase in a height dimension in the anterior direction. Although the depicted embodiment includes three (3) steps, those of ordinary skill in the art will understand that any suitable number of steps may be provided to achieve the desired increase in height and rate of increase in height.

A posterior surface 56 of head portion 42 may be substantially planar with the exception of a one or more tabs 58 protruding posteriorly therefrom. Although the depicted embodiments illustrate only one tab 58 protruding from posterior surface 56, those of ordinary skill in the art will understand that any suitable number of tabs 58 may protrude from the posterior surface 56. Tab 58 may include any suitable dimension and/or configuration. As will be discussed in greater detail below, tab 58 may facilitate connection of first component 24 to second component 60. Rather than including a protruding tab 58, head portion 42 may include a recess (not shown) for receiving a correspondingly configured insert portion (not shown) extending from second component 60.

A lateral surface, e.g., outer lateral surface 62 of head portion 42 may be substantially planar. In some embodiments, lateral surface 62 may include at least one geometric feature 64 for allowing a tool to grip or otherwise manipulate assembly 10. Geometric feature 64 may include any suitable configuration corresponding to an appropriate tool. In one embodiment, geometric feature 64 may include a substantially rectangular notch having rounded corners. The notch may include a depth into the lateral surface 62 of head portion 42. As shown in FIG. 1A, geometric feature 64 may be disposed relatively closer to posterior surface 56 than to anterior surface 66 of head portion 42.

Anterior surface 66 of head portion 42 may be substantially planar. In some embodiments, anterior surface 66 may include at least one counterbore 68 configured to at least partially receive a head of a fastener, which will be described in greater detail below. Counterbore 68 may be in communication with a coaxial hole extending through head portion 42, as shown in FIG. 1D. Counterbore 68 may be configured to facilitate guiding a fastener (e.g., bone screw 80 described in greater detail below) through head portion 42 at a desired angle. In an embodiment, counterbore 68 and its corresponding coaxial hole may be configured to guide the fastener into a vertebral body in a converging relationship relative to the fastener associated with head portion 42a. The angle of insertion can be varied between 35 degrees from the cephalad caudal direction to 10 degrees medial-lateral.

Head portion 42 may include a second counterbore 70 disposed adjacent to counterbore 68. Second counterbore 70 also may be in communication with another coaxial hole (not shown), which may not necessarily extend all the way through head portion 42. Indeed, in the depicted embodiment, second counterbore 70 is in communication with a blind coaxial hole. Further, second counterbore 70 may be in communication with counterbore 68. Stated another way, a portion of second counterbore 70 may open into counterbore 68 and vice versa, as shown in FIG. 1A. As will be explained in greater detail below, second counterbore 70 may include a fastener restricting mechanism 72. Second counterbore 70 may include a depth sufficient to allow fastener restricting mechanism 72 to be disposed completely within second counterbore 70 or at least flush with anterior surface 66 of head portion 42.

Fastener restricting mechanism 72 may be any suitable mechanism for preventing a fastener, such as, e.g., bone screw 80, from becoming disengaged from the vertebral body to which it is secured. For example, in one embodiment, fastener restricting mechanism 72 may be configured to limit longitudinal displacement of bone screw 80. Fastener restricting mechanism 72 may include a screw (e.g., a set screw) disposed in a hole that is coaxial with second counterbore 70. In some embodiments, fastener restricting mechanism 72 may include a cam-style blocking mechanism. For example, the fastener restricting mechanism 72 may include a screw having a head having a greater width dimension than a remainder of the screw. The head of mechanism 72 may include a cutout that allows a head 82 of bone screw 80 to freely pass the head of mechanism 72 when the cutout is disposed in the path of travel of head 82. However, when fastener restricting mechanism 72 is rotated, the cutout may be moved away from the path of travel of head 82 and a blocking portion of mechanism 72 may be disposed in the path of travel of head 82, thereby preventing longitudinal movement of bone screw 80. Also, as is known in the art, the head 82 of bone screw 80 may include a keyed opening 81, which may be configured to receive a correspondingly-sized tool for rotating bone screw 80.

As explained above, second leg 28 may include one or more features of leg 26. Indeed, in some embodiments, second leg 28 may be an identical mirror image of first leg 26.

In some embodiments, portions of first component 24 may be configured to promote bone tissue infiltration. For example, in one embodiment, the superior and inferior surfaces (or any other surfaces configured to be in contact with bony tissue) may include a porous configuration to allow bone ingrowth. In another embodiment, those surfaces of first component 24 that are intended to be in contact with bony tissue may include a suitable coating, such as, e.g., hydroxyapatite, for promoting bone tissue ingrowth into portions of first component 24.

First component 24 may be fabricated via any method known in the art. For example, first component 24 (including first leg 26, second leg 28, and connecting leg 30) may be molded in a one-piece configuration. In another embodiment, portions of first component 24 may be discreetly fabricated, and then secured together by any suitable means, including, but not limited to, welding.

First component 24 may be fabricated from any suitable biocompatible material. For example, in one embodiment, all or a portion of first component 24 may be made of Titanium. Other suitable materials include, but are not limited to, stainless steel, nickel, silver, or any suitable alloy.

As alluded to above, outer member 20 may further include a second component 60. As shown in FIG. 1A, for example, second component 60 may be disposed substantially about first component 24. More particularly, second component 60 may extend from posterior surface 56 of head portion 42, along first leg 26, along connecting leg 30, and along second leg 28 to the posterior surface 56a of second head portion 42. In some embodiments, second component 60 may be formed of a one-piece configuration. In other embodiments, second component 60 may be formed of a plurality of discrete components secured to one another.

With continuing reference to FIG. 1A, the portions of second component 60 adjacent head portions 42, 42a, may include an opening or a cutout 74 configured to receive tab 58 therein. Cutout 74 may include any suitable configuration corresponding to a configuration of tab 58. In one embodiment, cutout 74 may be configured to retain tab 58 therein via a suitable interference or friction fit. In another embodiment, tab 58 may be retained within cutout 74 with the aid of an adhesive. In an even further embodiment, a mechanical fastener 76 may be used to retain tab 58 within cutout 74. In those embodiments where a mechanical fastener 76 may be used, one of a superior or inferior surface of second component 60 may include an opening 78 for receiving the fastener 76. The opening 78 may include a counterbore configured to completely receive a head of fastener 76 therein. The counterbore 78 may lead to a coaxial opening extending through second component 60 at least between the counterbore and cutout 74. In such embodiments, tab 58 may include a corresponding opening or hole (not shown) for receiving a portion of fastener 76 therein. In addition, both the hole in tab 58 and the coaxial hole through second component 60 may include geometric features (e.g., internal screw threads) configured to interact with corresponding geometric features (e.g., external screw threads) on fastener 76 for retaining fastener, thereby retaining tab 58 within cutout 74.

Figure 1B:
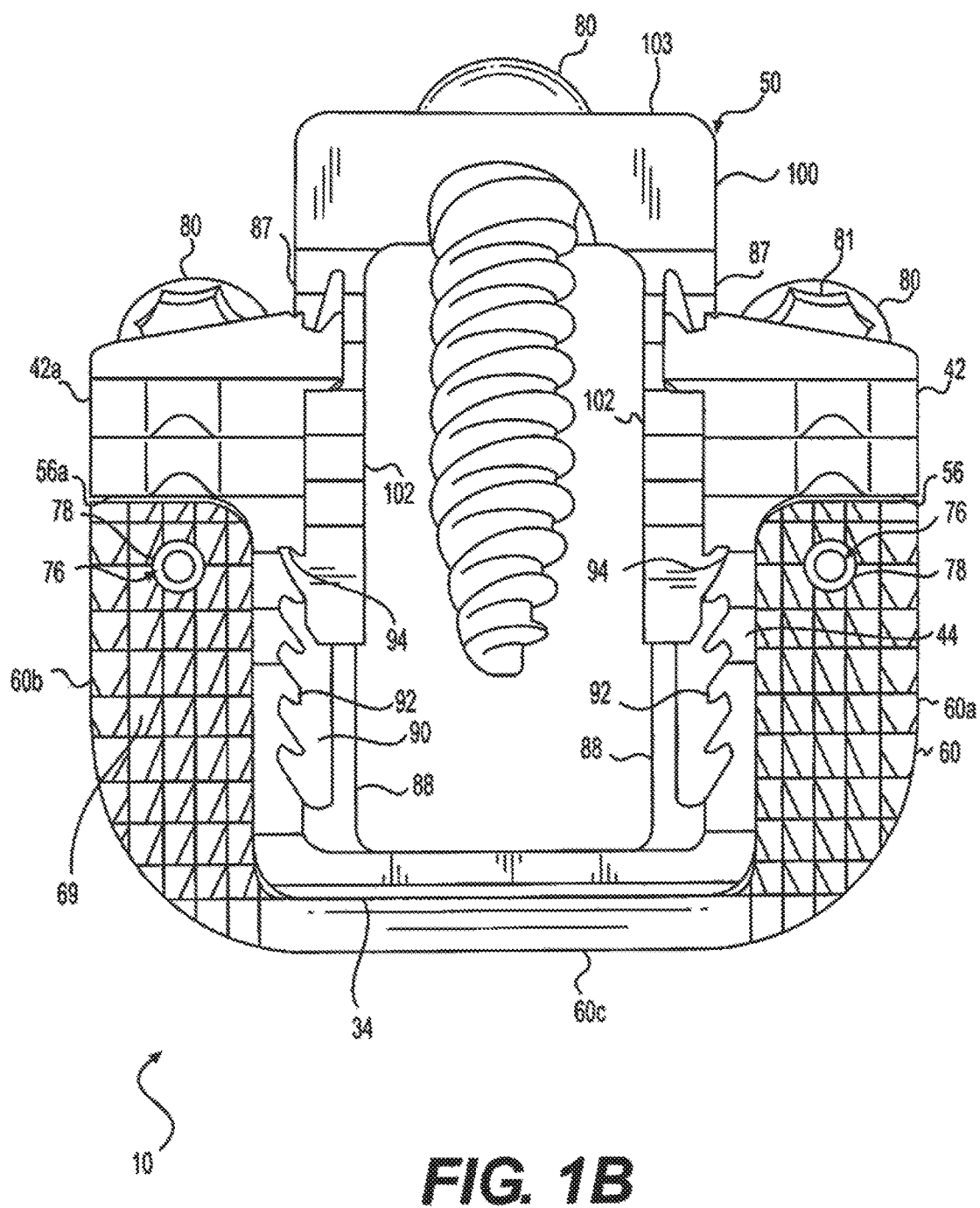
FIG. 1B depicts a top view of the apparatus of FIG. 1A.
Figure 1C:
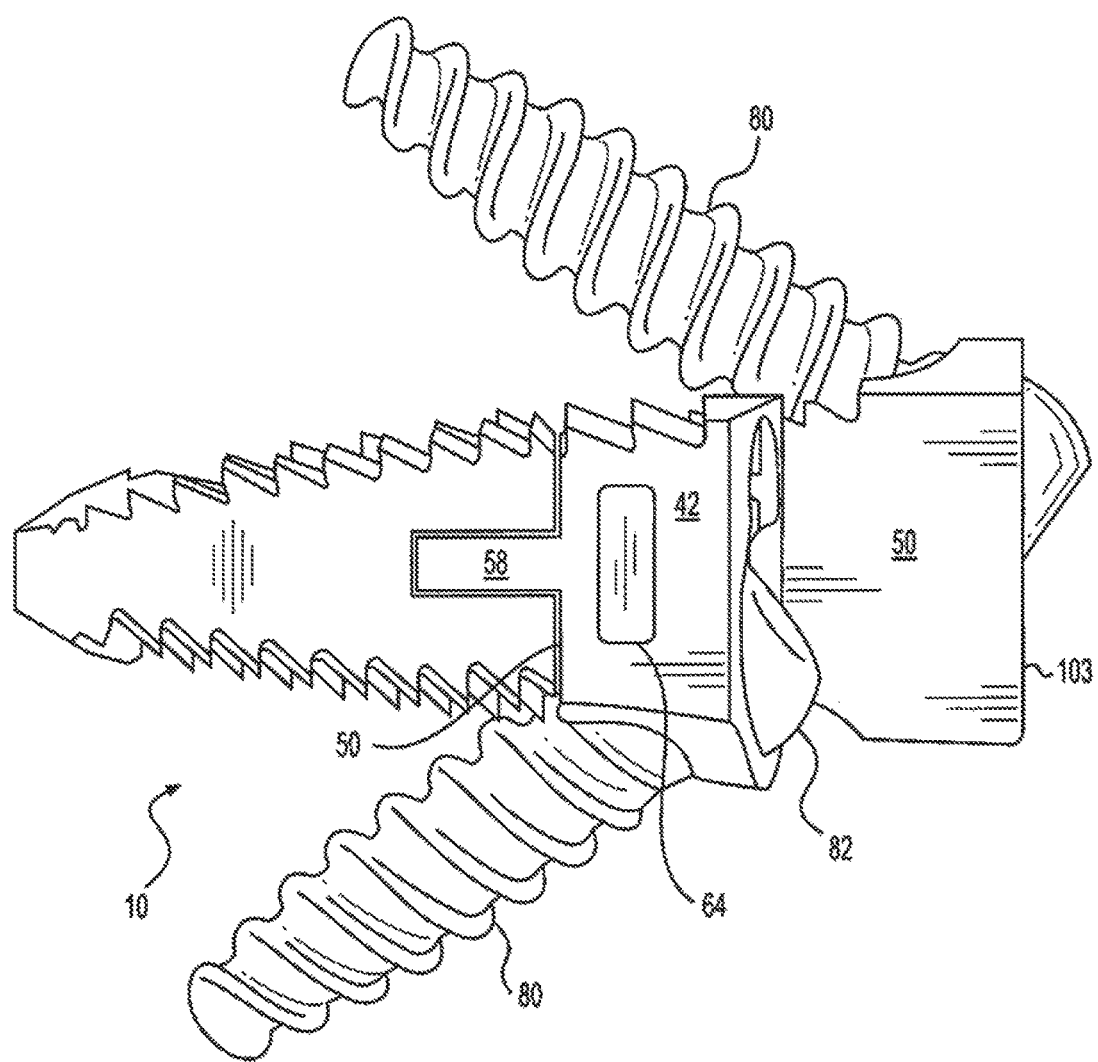
FIG. 1C depicts a side view of the apparatus of FIG. 1A.
Figure 1D:
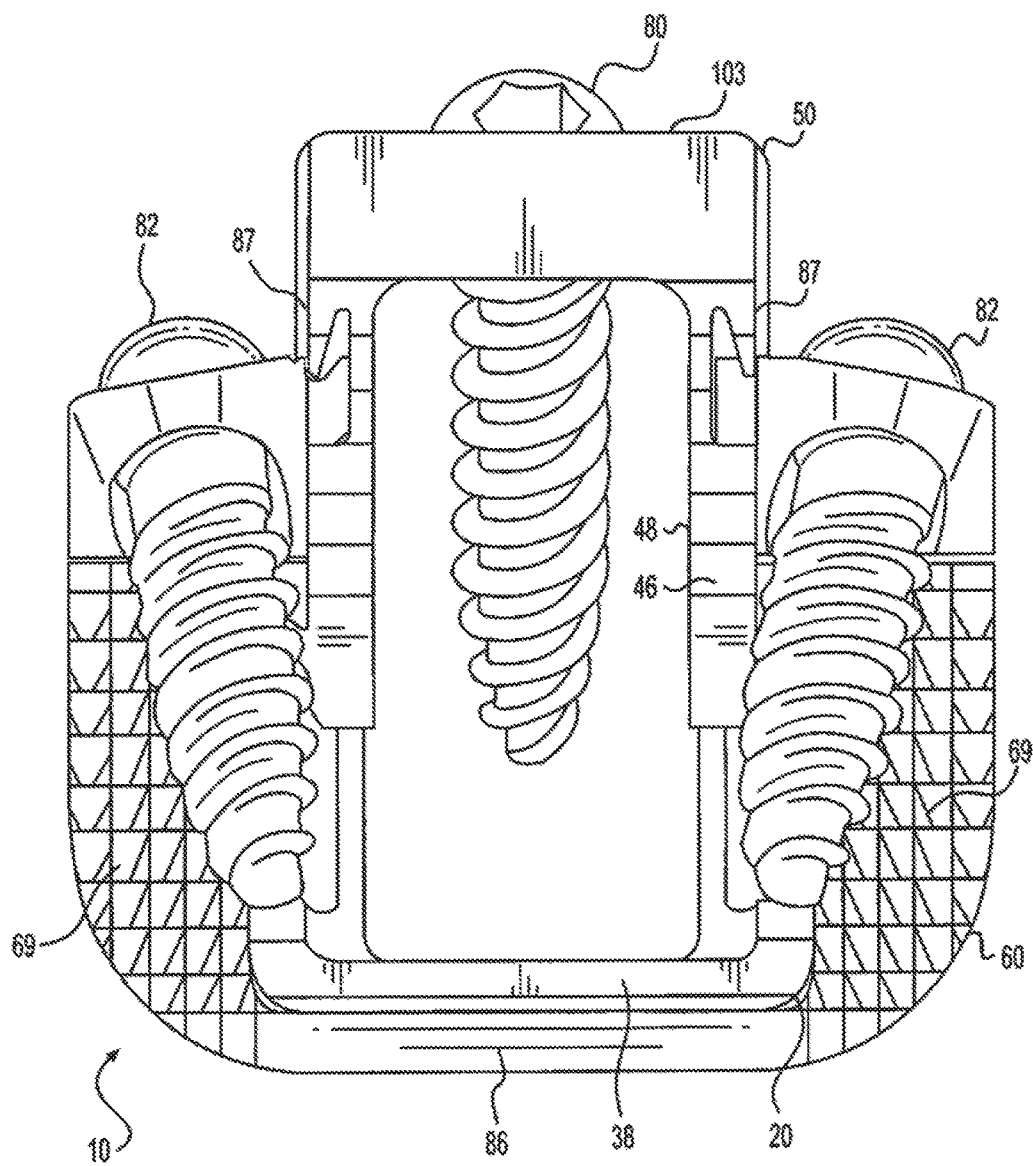
FIG. 1D depicts a bottom view of the apparatus of FIG. 1A.

As shown in FIG. 1B, second component 60 may include first and second lateral portions 60a, 60b corresponding to head portions 42, 42a. Anterior portions of lateral portions 60a, 60b may include width and height dimensions corresponding approximately to those of head portions 42, 42a. In addition, as shown in FIG. 1A, lateral portions 60a, 60b may include a posteriorly tapering configuration. That is, a height of lateral portion 60 at, e.g., a location adjacent head portion 42 may be larger than a height at, e.g., a location farther away from head portion 42.

The superior and/or inferior surfaces of lateral portions 60a, 60b may include one or more geometric configurations configured to promote frictional interaction with adjacent bone or tissue surfaces. For example, the superior and/or inferior surfaces may include a plurality of pyramid-like projections 69 and corresponding valleys. In other embodiments, the superior and/or inferior surfaces may include, but are not limited to, barbs, tines, hooks, a roughened surface, etc. In addition, or alternatively, the superior and/or inferior surfaces may include a suitable porous structure configured to promote bone ingrowth. In addition, the superior and/or inferior surfaces may include a coating for promoting bone ingrowth. In one embodiment, the coating may include hydroxyapatite. Of course, any portion of assembly 10 may include any suitable coating, including, but not limited to, coatings containing therapeutic, antibiotic, and/or anesthetic agents.

Lateral portions 60a, 60b may be connected to one another via central portion 60c. Central portion 60c may be disposed adjacent connecting leg 30. Central portion 60c may include width and height dimensions substantially similar to connecting leg 30. In one embodiment, the superior 84 and anterior 86 surfaces of central portion 60c may include a tapering configuration. Further, although the depicted embodiments do not illustrate any geometric features on the surfaces of central portion 60c, those of ordinary skill will readily recognize that one or more surfaces of central portion 60c may include any suitable geometric configurations and/or coatings.

Second component 60 may be made of any suitable biocompatible materials, including, but not limited to, thermoplastics, metals, composites, and/or alloys. In one embodiment, for example, second component 60 may be made of polyether ether ketone (PEEK).

With renewed reference to FIG. 1A, for example, inner surfaces of legs 26 and 28 may be substantially planar. In one embodiment, however, the inner surfaces of one or both of legs 26 and 28 may include a ledge or rail 88 disposed thereon. As will be discussed in greater detail below, rail 88 may be configured to slidably receive inner member 50. In some embodiments, rail 88 may be integrally fabricated with the inner surfaces of legs 26 and 28. In another embodiment, rail 88 may be secured to the inner surfaces of legs 26 and 28 via any suitable means. Although the depicted embodiment illustrates only one rail 88 on each of the inner surfaces of legs 26 and 28, those of ordinary skill in the art will readily understand that any suitable number of rails 88 may be provided in accordance with the principles of the present disclosure. In some embodiments, instead of or in addition to a rail 88, the inner surfaces of legs 26 and 28 may be formed with a groove 77 for receiving a corresponding projection 79 from inner member 50. The groove 77 may be integrally formed within the surfaces of legs 26 and 28, or the groove may be cut (by, e.g., a laser) after legs 26 and 28 are formed. Moreover, although the depicted embodiment illustrates that a rail 88 is provided on each of legs 26 and 28, some embodiments may only include a single rail 88 provided on one of legs 26 and 28. In further embodiments, one of legs 26 and 28 may include a rail 88, and the other of legs 26 and 28 may include a groove 77 as discussed above.

In addition to a mechanism (e.g., rail 88) for slidably receiving inner member 50, the inner surfaces of one or both of legs 26 and 28 may include a mechanism for retaining a position of inner member 50 relative to outer member 20. The mechanism for retaining inner member 50 relative to outer member 20 may be any suitable mechanism known in the art. For example, in one embodiment, the inner surfaces of one or both of legs 26 and 28 may include a ratchet mechanism 90, which will be discussed below in greater detail. In another embodiment, the mechanism may include one or more spring-loaded projections (not shown) configured to interact with a plurality of grooves or openings (not shown). The spring-loaded projections may be disposed on inner surfaces of legs 26 and 28, and the grooves may be disposed on inner member 50, and vice versa.

In some embodiments, the mechanism for retaining a position of inner member 50 relative to outer member 20 may be configured to allow only unidirectional movement of inner member 50 relative to outer member 20. For example, ratchet mechanism 90 may comprise of plurality of directional teeth 92 disposed on an inner surface of one of legs 26 and 28. In addition, one or more pawls or other suitable catch(es) 94 may be disposed on (e.g., extend from) inner member 50. The positioning of the directional teeth 92 and catch(es) 94 may be reversed in some embodiments. In addition, the ratchet mechanism 90 may include multiple rows of directional teeth 92. As will be explained in greater detail below, ratchet mechanism 90 may allow inner member 50 to be gradually and progressively advanced into opening 22, while precluding inner member 50 from being withdrawn in the reverse direction.

Figure 2A:
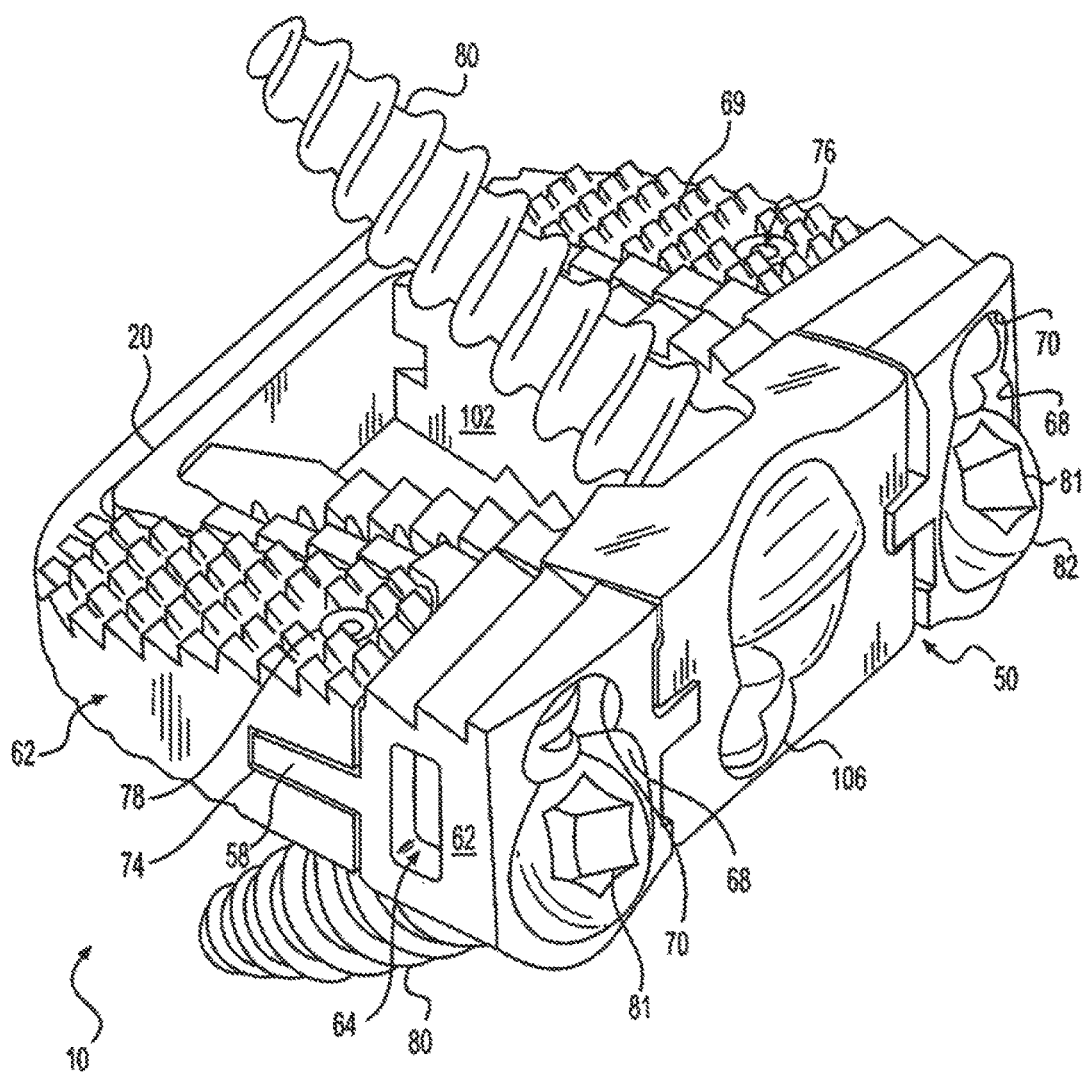
FIG. 2A depicts an isometric view of the apparatus of FIG. 1A in a second configuration, in accordance with an embodiment of the present disclosure.

With continued reference to FIGS. 1A-1D, inner member 50 may be configured to be at least partially received within opening 22 of outer member 20. Inner member 50 may include an anterior portion 100 with a plurality of legs 102 extending posteriorly away from anterior portion 100. In one embodiment, the entirety of inner member 50 may be configured to be received within opening 22, such that anterior portion 100 is made flush with head portions 42, 42*a*, as shown in FIG. 2A. For the purposes of efficiency, only one of the plurality of legs 102 will be described herein. However, those of ordinary skill in the art will understand that the other leg 102 may include any or all of the described features. Indeed, in one exemplary embodiment, the plurality of legs 102 may be substantially identical mirror images of each another.

Anterior portion 100 may include an anterior surface 103. Anterior surface 103 may be substantially planar. In one embodiment, anterior surface 103 may include a first counterbore 104 and a second counterbore 106. The first counterbore 104 may be in communication with a coaxial hole (not shown), and may be configured to receive and retain a fastener, such as, e.g., bone screw 80, therein. For example, a portion of first counterbore 104 and or the coaxial hole may include geometric features (e.g., internal screw threads) configured to interact with geometric features (e.g., external screw threads) disposed on bone screw 80. As with counterbore 68 described above, first counterbore 106 may be configured to facilitate guiding a fastener (described in greater detail below) through anterior portion 100 at a desired angle.

The second counterbore 106 may be disposed adjacent and in communication with first counterbore 104. As described above, second counterbore 106 may include one or more features of counterbore 70. For example, second counterbore 106 may be in communication with a coaxial hole (e.g., a blind coaxial hole) (not shown), and may be configured to receive and retain a fastener retaining mechanism 72 (described above) therein.

In addition, anterior portion 100 may be dimensioned so that the superior and/or inferior surfaces are substantially flush with the respective surfaces of head portions 42, 42*a*, as shown in FIG. 2A, for example.

Legs 102 may extend posteriorly from a posterior surface of anterior portion 100, so as to define a substantially U-shaped configuration. In one embodiment, legs 102 may be fabricated from a one-piece construction with anterior portion 100. In another embodiment, one or both of legs 102 may be fixedly secured to a posterior surface of anterior portion 100, via, e.g., welding or a suitable fastening mechanism, including, but not limited to, a mechanical fastener or an adhesive. Legs 102 may generally include a tapering configuration corresponding to associated portions (e.g., legs 26, 28) of outer member 20. For example, legs 102 may decrease in height when moving in the posterior direction.

As alluded to above, one or both of legs 102 may include portions of ratchet mechanism 90. For example, one or both of legs 102 may include either a plurality of directional teeth 92 or catches 94. In the illustrated embodiments, legs 102 include a single catch 94 extending laterally away from legs 102, as shown in FIG. 1B. The catch 94 may include a hook-like configuration. Catch 94 may be configured to deform out of and into engagement with successive teeth 92. Accordingly, a portion of catch 94 may be elastic or spring-like. In some embodiments, legs 102 may include a plurality of catches 94. The catch 94 may be configured to interact with directional teeth 92 to retain inner member 50 relative to outer member 20. As explained above, catch 94 may be configured to allow unidirectional relative movement between outer member 20 and inner member 50. That is, directional teeth 92 and catch 94, collectively referred to as ratchet mechanism 90, may be configured to only allow inner member 50 to move into opening 22, but not out of it.

In addition, each of legs 102 may include an elastic or spring-like stabilizing member 87. The stabilizing member 87 may assist in guiding inner member 50 as it slides relative to outer member 20. In addition, stabilizing member 87 may be configured to exert tension against legs 26, 28, respectively, to ensure inner member 50 remains centered with respect to opening 22. Further, stabilizing member 87 may also act as a spring point for ratchet mechanism 90, allowing for a smooth flexing of catch 94.

The superior and/or inferior surfaces of inner member 50 may be configured to promote bone ingrowth. For example, one or more superior and/or inferior surfaces of inner member 50 may include a porous structure to facilitate tissue infiltration. In addition, the one or more superior and/or inferior surfaces of inner member 50 may include any suitable coating, such as, e.g., a coating of hydroxyapatite, a therapeutic agent, and/or an anesthetic.

The sides of inner member 50 may include one more slots and/or notches 110, and/or projections 79, which may be configured to allow inner member 50 to slide on rail 88 of outer member 20. Of course, those of ordinary skill in the art will recognize that the exact design and configuration of the mechanism that allows inner member 50 to move relative to outer member 20 may vary among the many available options known in the art. The illustrated embodiments and configurations therefore are only for exemplary purposes. For example, as shown in FIG. 1A, each side of inner member 50 includes two notches 110, at least one of which is configured to matingly receive rail 88. In addition, a projection 79 may be configured to be received into a groove 77. The notches 110 may be disposed along an entire side of inner member 50, and may be disposed on an outer sidewall of legs 102. In embodiments where the inner surfaces of legs 26 and 28 include multiple projections or rails, e.g., the outer sidewall of legs 102 would include corresponding geometric features as well.

Figure 2B:
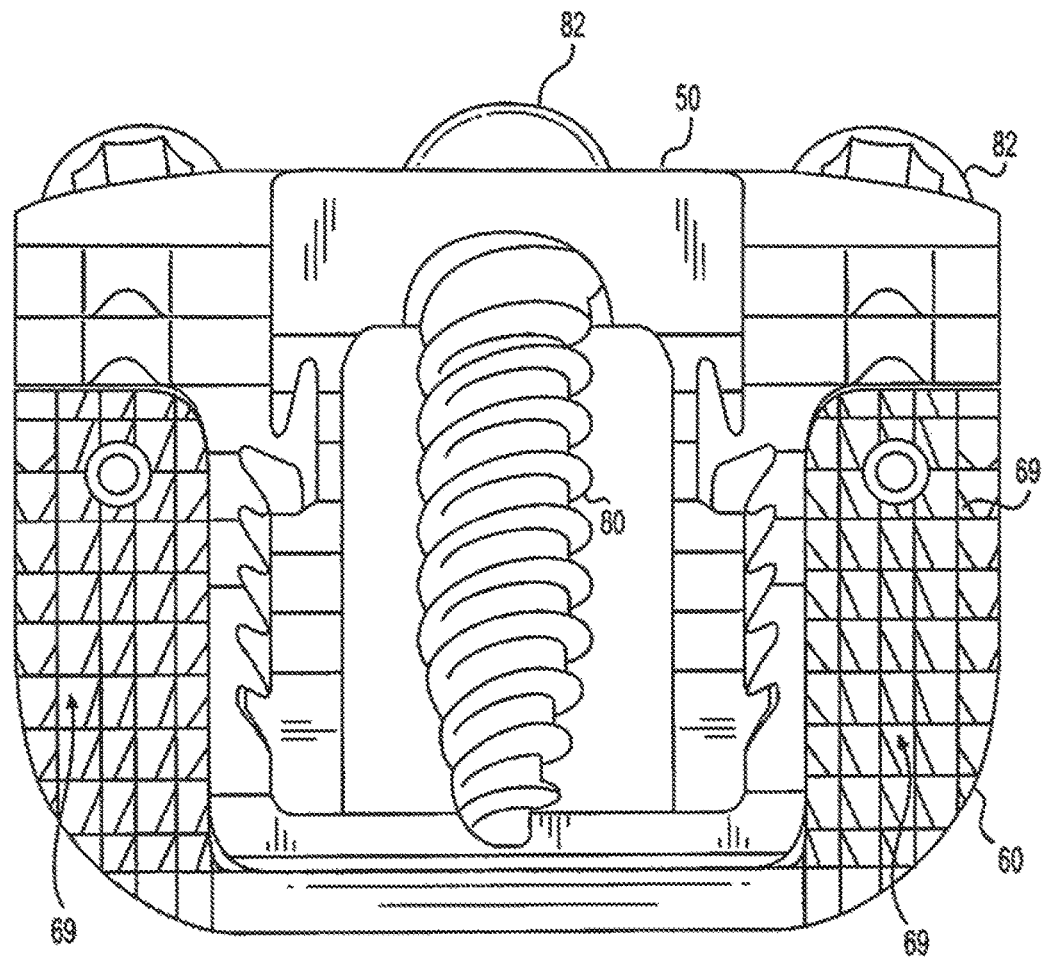
FIG. 2B depicts a top view of the apparatus of FIG. 2A.

With reference now to FIGS. 2A and 2B, as discussed above, inner member 50 is configured to move relative outer member 20, such that it may gradually move from the configuration depicted in FIGS. 1A-1D to, e.g., the configuration depicted shown in FIGS. 2A-2B. As a result of ratchet mechanism 90, however, inner member 50 may be positioned in any intermediate position between those shown in FIGS. 1A-1D and FIGS. 2A-2B. As shown in FIG. 2A, inner member 50 may be dimensioned to be completely received within opening 22, so that anterior surface 102 is substantially flush with the anterior surfaces of head portions 42, 42a. As will be discussed below in greater detail, inner member 50 may be moved relative to outer member 20 by any suitable method. For example, in one embodiment, inner member 50 may be moved by driving its associated screw 80 into a vertebral body. In another embodiment, the inner member 50 may be pushed into opening 22 by, e.g., a tool, until inner member 50 is positioned in a desired location relative to outer member 20. Subsequently, a screw 80 may be inserted into counterbore 104 and secured to a vertebral body, thereby securing inner member 50 relative to outer member 20.

Furthermore, portions of inner member 50 and/or outer member 20 may be radiolucent or radiopaque as desired. In addition, assembly 10 may include any suitable radiopaque markings necessary to assist with visualizing assembly 10 within a patient's body.

Figure 3A:
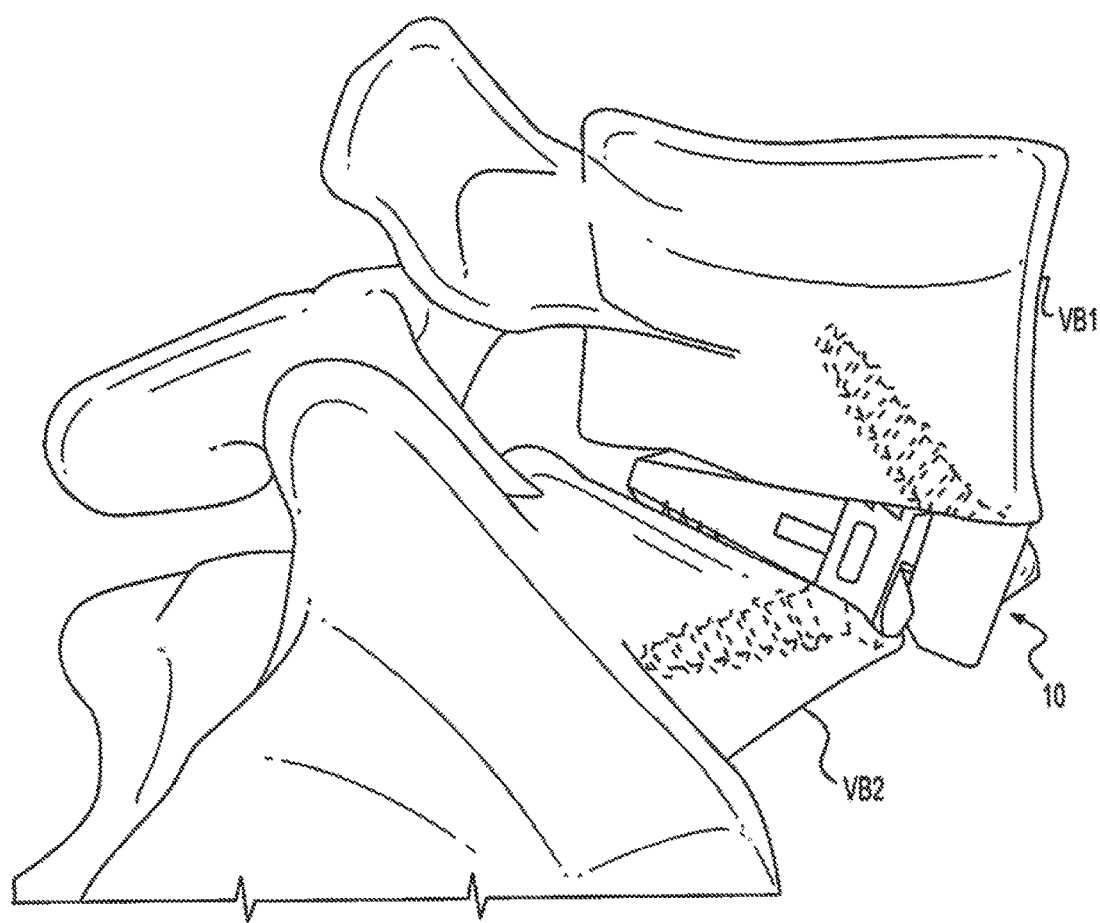
FIG. 3A depicts the apparatus of FIG. 1A implanted between two vertebral bodies, in accordance with an embodiment of the present disclosure.
Figure 3B:
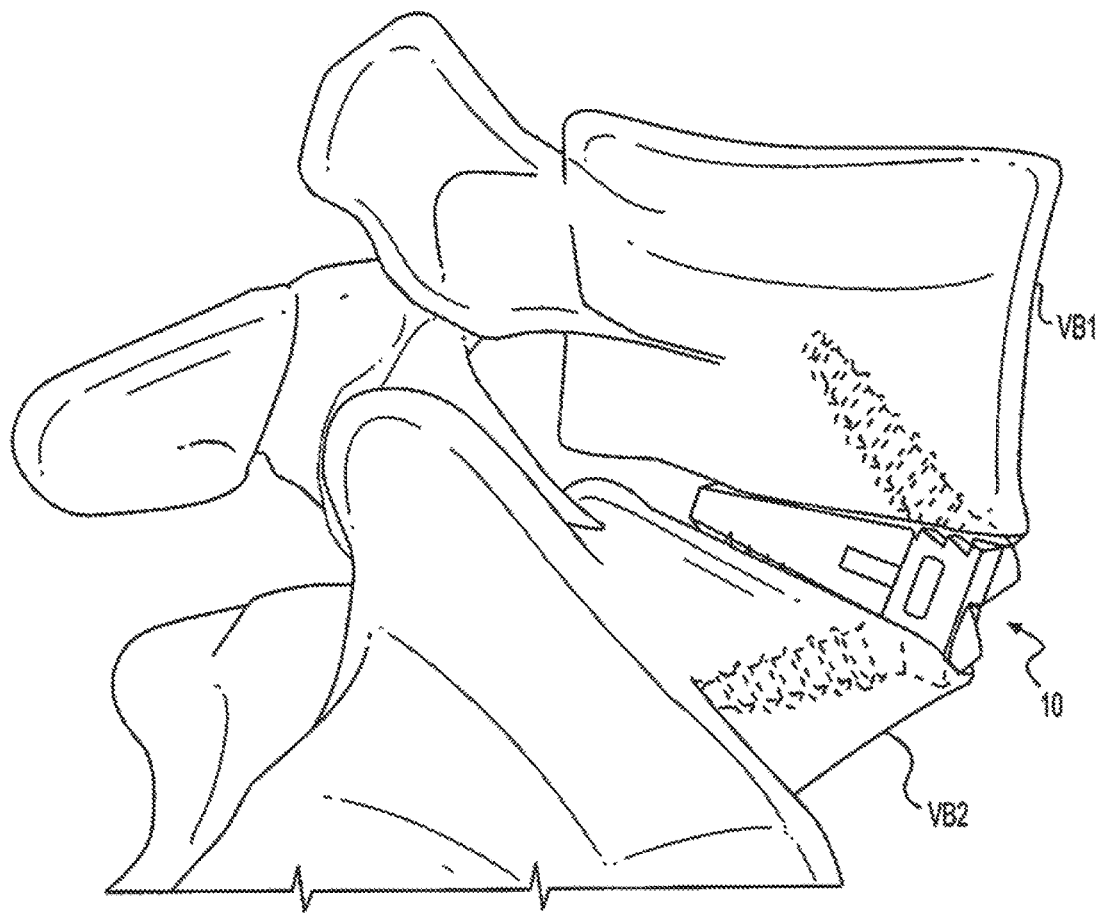
FIG. 3B depicts the apparatus of FIG. 1A adjusted to be in the second configuration of FIG. 2A, in accordance with an embodiment of the present disclosure.

Turning now to FIGS. 3A-3B, an exemplary method for correcting misalignment of vertebral bodies in a patient's spine is depicted and described herein. As shown in FIG. 3A, a first vertebral body VB1 may have slipped forward and out of alignment relative to a second vertebral body VB2 disposed below first vertebral body VB1. Such slippage may occur for any number of reasons, including, but not limited to, age-related degeneration, physical trauma, congenital birth defect, or stress fractures caused by, among other things, excessive hyperextension of the spine.

Prior to beginning a procedure to correct the misalignment between vertebral bodies VB1 and VB2, a physician or other healthcare provider may manually move vertebral body VB1 into correct alignment to gauge, among other things, the amount of correction needed and the appropriate positioning of assembly 10 relative to vertebral body VB2. To correct the aforementioned vertebral body misalignment, the physician or other healthcare provider may begin by accessing the targeted anatomical structures through any suitable approach known in the art. It is contemplated that the devices described herein may allow for correcting vertebral misalignment via a solely anterior approach. Once the physician accesses the targeted anatomical structures, he/she may begin by removing the native disk disposed in between of vertebral bodies VB1 and VB2. Vertebral bodies VB1 and VB2 may include any vertebral bodies in a patient's spine. In some cases, vertebral body VB1 may include the Lumbar 5 (L5) vertebral body, and vertebral body VB2 may include the Sacrum 1 (S1) vertebral body. The disk may be removed by any suitable procedure known in the art, including, but not limited to, a discectomy. In some instances, the physician may roughen adjacent surfaces on each of vertebral bodies VB1 and VB2 prior to positioning assembly 10 in the interbody disk space between vertebral bodies VB1 and VB2. Assembly 10 may be implanted in a pre-assembled stated with inner member 50 connected to outer member 20. Further, during the procedure, the assembly 10 may not be disassembled. As alluded to above, the procedure may be conducted via an anterior-only approach. That is, the assembly 10 may be implanted and manipulated from only an anterior side of the patient.

Once positioned appropriately on, e.g., vertebral body VB2, the physician may use a tool (not shown) to engage opening 81 on the associated screws 80 to drive screws 80 into vertebral body VB2 at a predetermined angle, so as to securely fasten outer member 20 to vertebral body VB2. Prior to engaging screws 80, however, if necessary, the physician may manipulate fastener restricting mechanism 72 to a configuration that allows screw heads 82 to pass by fastener restricting mechanism 72. As shown in, e.g., FIG. 1D, screws 80 may be inserted into vertebral body VB2 in a converging relationship relative to one another. Once the screws 80 have properly secured outer member 20 to vertebral body VB2, the fastener restricting mechanism 72 may be manipulated again to prevent screws 80 from becoming disengaged. Next, in some embodiments, bone cement or another similar substance may be placed within opening 22 of outer member 20. Subsequently, in one embodiment, inner member 50 may be manually pushed into cavity to effect the desired amount of correction necessary to correct the misalignment of vertebral bodies VB1 and VB2. As noted above, inner member 50 may be gradually and step-by-step advanced into opening 22 as catch 94 passes each directional tooth 92. In another embodiment, bone screw 80 associated with inner member 50 may be gradually advanced into vertebral body VB1 until the desired level of correction is achieved, as shown in FIG. 3B. Once the desired level of correction is achieved, a fastener restricting mechanism 72 may be activated to prevent bone screw 80 of inner member 50 from becoming disengaged.

With reference now to FIGS. 4A-4F, there are depicted additional embodiments of devices for correcting misalignment of vertebral bodies, including, e.g., spondylolisthesis. Though the depicted embodiments contemplate treating spondylolisthesis via an anterior approach, those of ordinary skill in the art will understand that any suitable approach is contemplated within the principles of the present disclosure. As noted above, each of the various embodiments disclosed herein may include any of the features described in connection with the other embodiments.

Figure 4A:
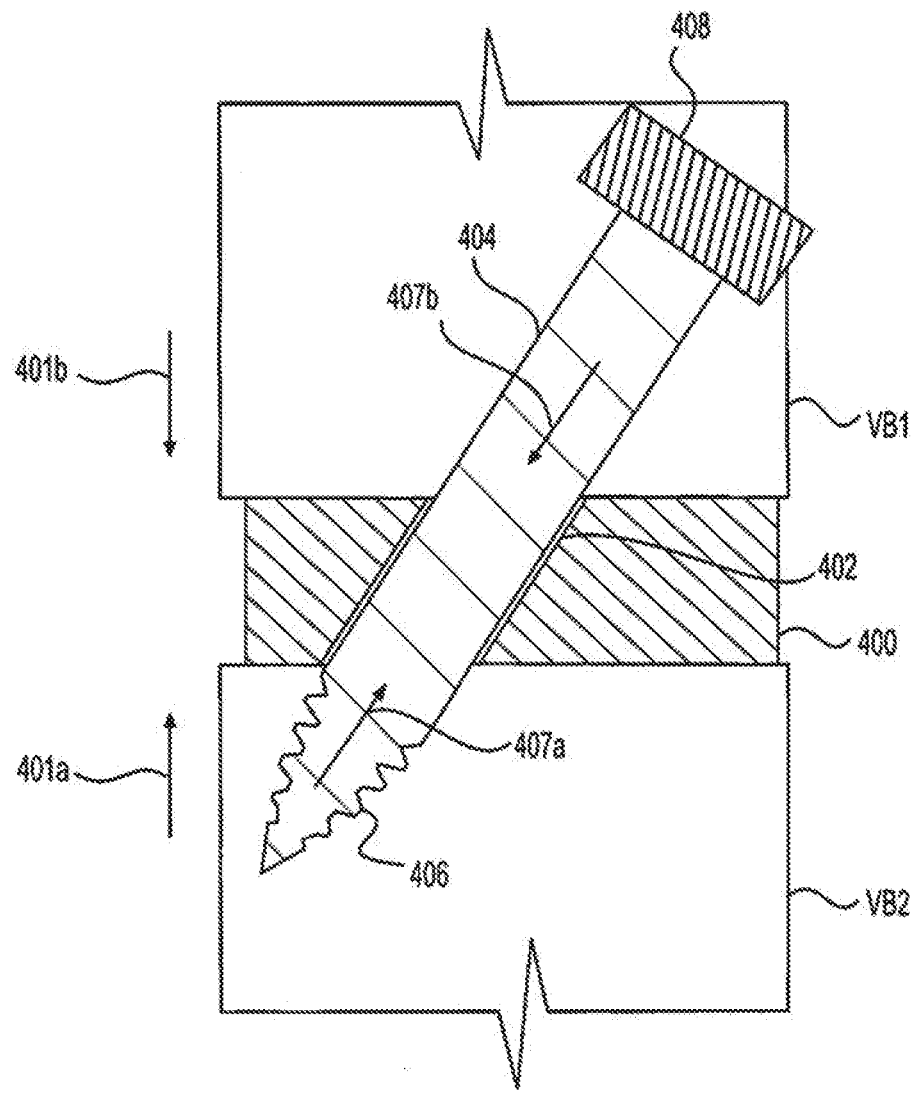
FIG. 4A depicts an apparatus for correcting misalignment of adjacent vertebral bodies, in accordance with a further embodiment of the present disclosure.

With specific reference to FIG. 4A, there is depicted a first vertebral body VB1 and a second vertebral body VB2. In the illustrated embodiment, first vertebral body VB1 may be disposed above second vertebral body VB2. An embodiment of a device in accordance with the present disclosure may include an interbody spacer 400 configured to be implanted within the interbody disk space between vertebral bodies VB1 and VB2. Spacer 400 may include any suitable configuration. In one embodiment, spacer 400 may include dimensions corresponding to first and second vertebral bodies VB1 and VB2. In addition, spacer 400 may include a substantially solid component made of, e.g., PEEK. In other embodiments, spacer 400 may include a cage-like configuration with a substantially hollow interior. For example, spacer 400 may be made of a plurality of wires defining an enclosure. The wires, or any portion of spacer 400, may be made of any suitable materials, including, e.g., titanium, nickel, stainless steel, or any alloys thereof.

In one embodiment, one or more of the superior and/or inferior surfaces of spacer 400 may include one or more geometric features configured to allow spacer 400 to grip adjacent bony surfaces of vertebral bodies VB1 and VB2. For example, the superior and/or inferior surfaces may include projections, such as, e.g., barbs, tines, spikes, and/or screws. In a further embodiment, the superior and/or inferior portions of spacer 400 may be configured to promote bone ingrowth. For example, one or both of the superior and/or inferior surfaces of spacer 400 may include a porous portion. In another embodiment, one or both of the superior and/or inferior surfaces of spacer 400 may include a suitable coating, including, e.g., a coating of hydroxyapatite. Spacer 400 may also include any other suitable coating (e.g., antibiotic, antiseptic, anesthetic, or otherwise therapeutic) known in the art. Further, spacer 400 may be flexible and/or compressible. In other embodiments, spacer 400 may be substantially rigid. A portion of spacer 400 may be radiopaque while other portions remain radiolucent. For example, in embodiments where spacer 400 is made of PEEK, the spacer 400 may include one or more suitable radiopaque markers thereon.

In some embodiments, one or more dimensions of spacer 400 may be selectively adjustable. For example, a height, width, or diameter of spacer 400 may be adjusted to suit a particular patient's anatomy. Spacer 400 may be adjusted by any means known in the art. In some embodiments, spacer 400 may be configured to expand and collapse. In such embodiments, spacer 400 may be expanded to desired dimensions. For example, spacer 400 may be an inflatable structure, which may be inflated until it expands to a desired dimension. In such cases, spacer 400 may be inflated with any suitable material. For example, spacer 400 may be inflated with a substance (e.g., an epoxy) configured to harden or cure once spacer 400 is inflated to a desired dimension.

Spacer 400 may include a passageway or channel 402 therethrough. Channel 402 may be formed by any suitable means known in the art. For example, spacer 400 may be molded with channel 402 therein. In another embodiment, channel 402 may be drilled or cut through spacer 400. Although the depicted embodiment illustrates a single channel 402, those of ordinary skill in the art will understand that spacer 400 may include any suitable number of channels 402. Channel 402 may extend through spacer 400 in any suitable direction or at any suitable angle. For example, channel 402 may extend at an angle configured to allow a fastener inserted therethrough to bring vertebral bodies VB1 and VB2 closer together. In addition, the angle may also cause the vertebral bodies to move laterally relative to one another. In those embodiments where a plurality of channels 402 are provided, the plurality of channels 402 may extend parallel to one another or at an angle relative to one another. One or all of the plurality of the channels 402 may be configured to receive a fastener such as, e.g., elongate member 404. Channel 402 may be preformed in spacer 400 prior to implantation. In some embodiments, however, channel 402 may be formed in spacer 400 after implantation. For example, a reamer (not shown) may be used to create channel 402. Alternatively, channel 402 may be created by advancing elongate member 404 through spacer 400.

With continued reference to FIG. 4A, the disclosed embodiment may further include an elongate member 404 inserted from vertebral body VB1 through spacer 400 and into vertebral body VB2. In some embodiments, elongate member 404 may include a strut, rod, or screw. That is, the elongate member 404 may have any suitable configuration known in the art. Elongate member 404 may include one or more geometric features for retaining elongate member 404 within vertebral bodies VB1 and VB2. Such features may include, e.g., screw threads and/or a screw head 408. In addition, a distal end of elongate member 404 may be sharpened or may terminate in a pointed end.

Elongate member 404 may be made of any suitable materials, including, e.g., titanium, stainless steel, nickel, or any suitable alloys. In addition, elongate member 404 may include tissue, such as, e.g., an allograft.

In the embodiment shown in FIG. 4A, a portion of vertebral body VB1 may be removed by, e.g., reaming. For example, a conventional reamer may be used to create a passageway into vertebral body VB1. Further, a cavity for accommodating screw head 408 may be also created in vertebral body VB1. In some embodiments, a passageway into vertebral body VB2 may be also created. In addition, a thread cap (not shown) may be secured to a base of the passageway in vertebral body VB2 for receiving elongate member 404.

In use, elongate member 404 may be inserted into vertebral body VB1, through spacer 400, and screwed into vertebral body VB2 with or without the aid of a suitable thread cap. Doing so will cause spacer 400 to become compressed between vertebral bodies VB1 and VB2, as indicated by arrows 401a and 401b. Also, as a result of the angle of insertion of elongate member 404, the vertebral bodies VB1 and VB2 may be moved laterally relative to one another to correct any misalignment caused by, e.g., spondylolisthesis, as shown by arrows 407a and 407b. The degree of correction necessary may determine the depth elongate member 404 is inserted into vertebral body VB2.

Figure 4B:
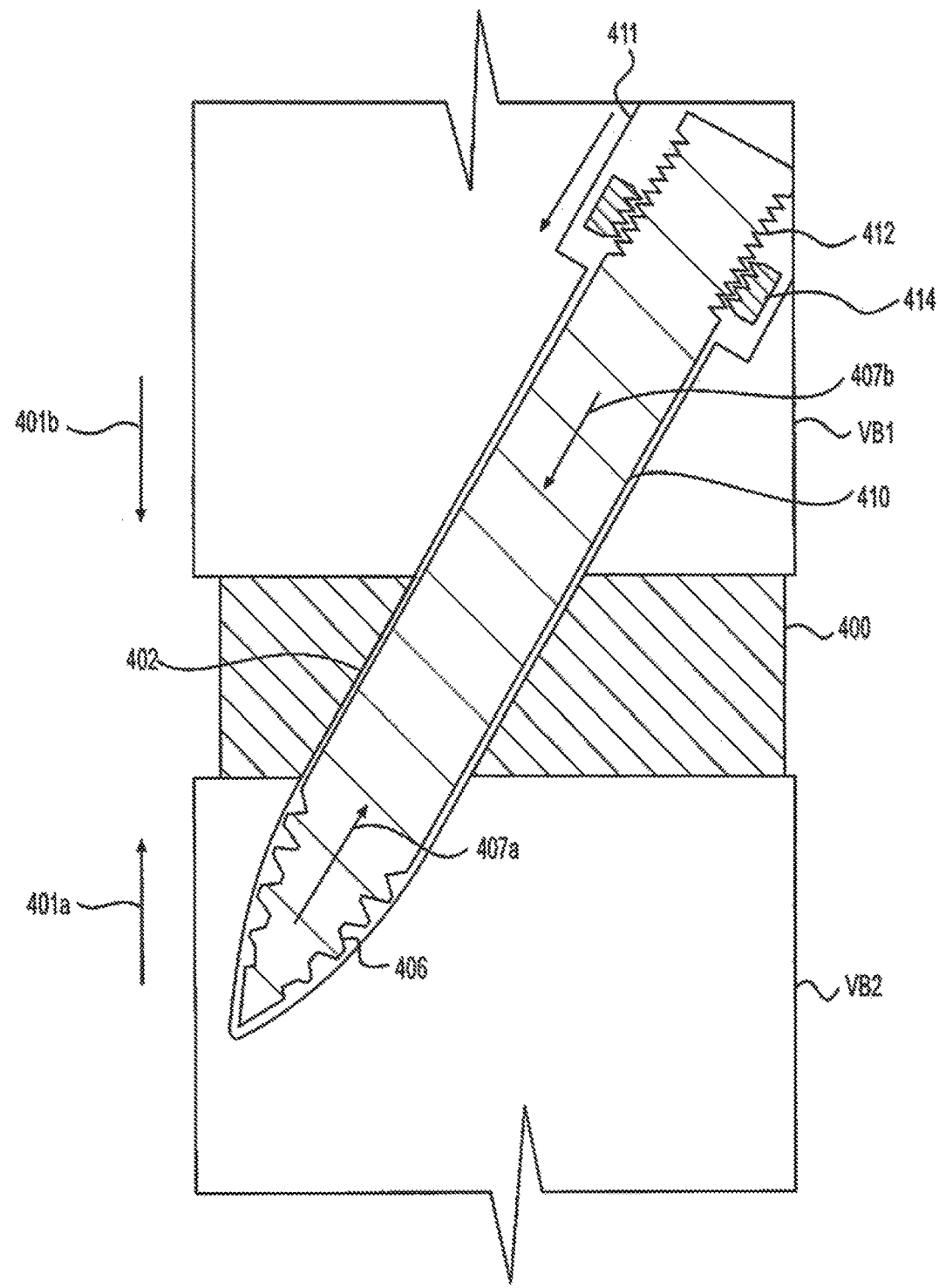
FIG. 4B depicts an apparatus for correcting misalignment of adjacent vertebral bodies, in accordance with another embodiment of the present disclosure.

With reference now to FIG. 4B, there is depicted another embodiment of a device for correcting vertebral body misalignment. The embodiment depicted in FIG. 4B may include one or more features of the embodiment depicted in FIG. 4A. For example, the embodiment of FIG. 4B may include a spacer 400 having a channel 402, and an elongate member 410. Elongate member 410 of FIG. 4B may be substantially similar to the elongate member 404. However, instead of a head 408, elongate member 410 may include screw threads disposed on both ends thereof, with at least one of the ends terminating in a pointed end, while the other terminates in a blunt end. The screw threads 412 on a superior end of elongate member 410 may be configured to receive a nut 414 thereon for securing elongate member 410 to vertebral body VB1. Nut 414 may include a through hole or a blind hole (not shown) therein. In embodiments where elongate member 410 may be secured to a vertebral body (e.g., vertebral body VB1) via nut 414, the vertebral body may be further reamed to create a counterbore 411 for receiving nut 414. As those in art will readily recognize, counterbore 414 may include a diameter large enough to completely accommodate nut 414 and the corresponding terminal end of elongate member 410 therein.

Figure 4C:
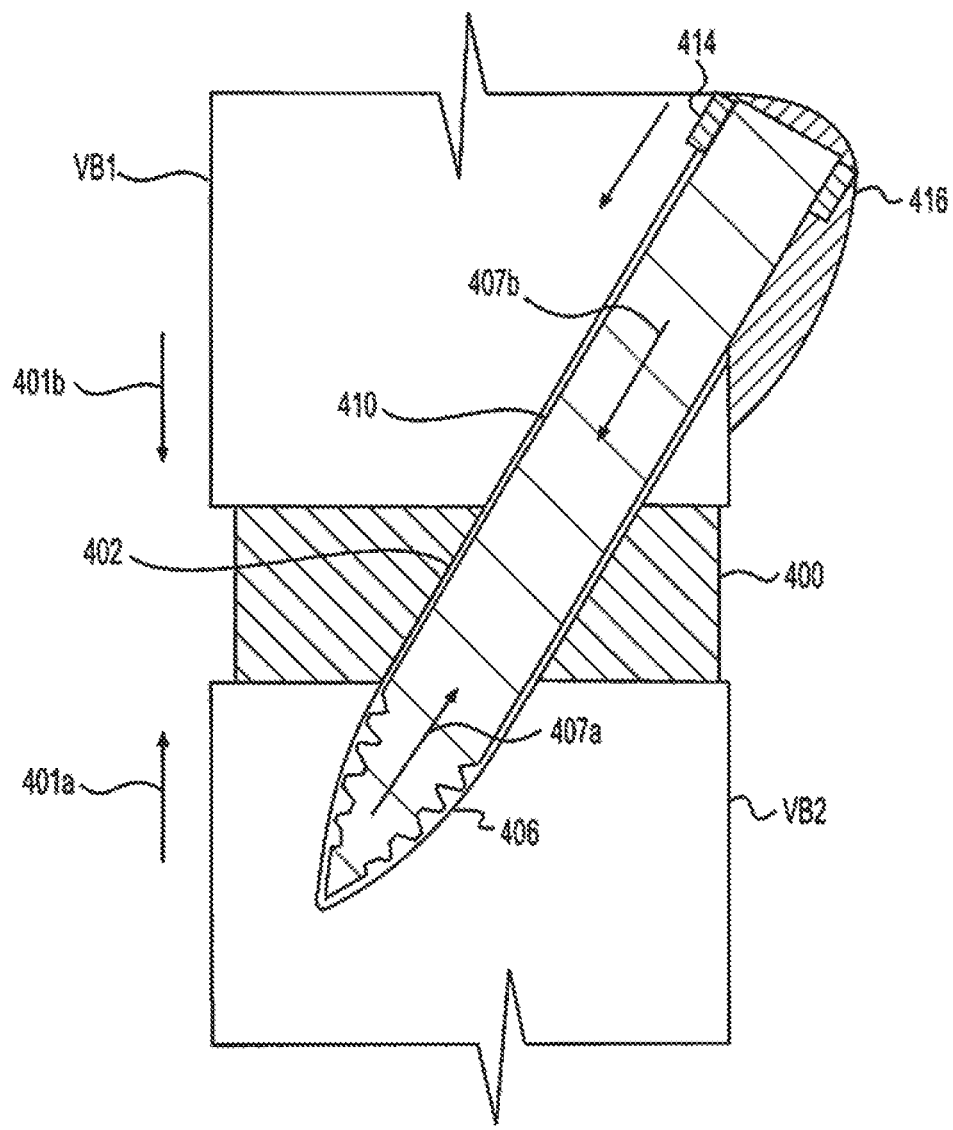
FIG. 4C depicts an apparatus for correcting misalignment of adjacent vertebral bodies, in accordance with yet another embodiment of the present disclosure.

With reference to FIG. 4C, an angle of channel 402 through spacer 400, or the depth elongate member 410 is inserted into vertebral body VB2, may cause a superior end of elongate member 410 to protrude out of a periphery of vertebral body VB1. In such cases, a cap 416 may be provided to protect anatomical structures (e.g., nerves, blood vessels, and the like) from damage caused by the superior end of elongate member 410 and/or an associated nut. Cap 416 may be any suitable structure configured for being disposed over an end of elongate member 410 to create a substantially atraumatic surface thereon. In one embodiment, cap 416 may define a cavity therein for placement over a superior end of elongate member 410. The cavity may be configured to receive the end of elongate member 410 and any associated nut. For example, cap 416 may be a rigid or flexible member configured to be cemented or otherwise secured over the superior end of elongate member 410. In a further embodiment, cap 416 may include a gel or paste-like substance configured to be applied about and over the superior end, and be molded or shaped to form an atraumatic external surface when dried or cured. The gel or paste-like substance may be configured to cure upon exposure to certain triggers, including, e.g., body chemistry and/or temperature.

Figure 4D:
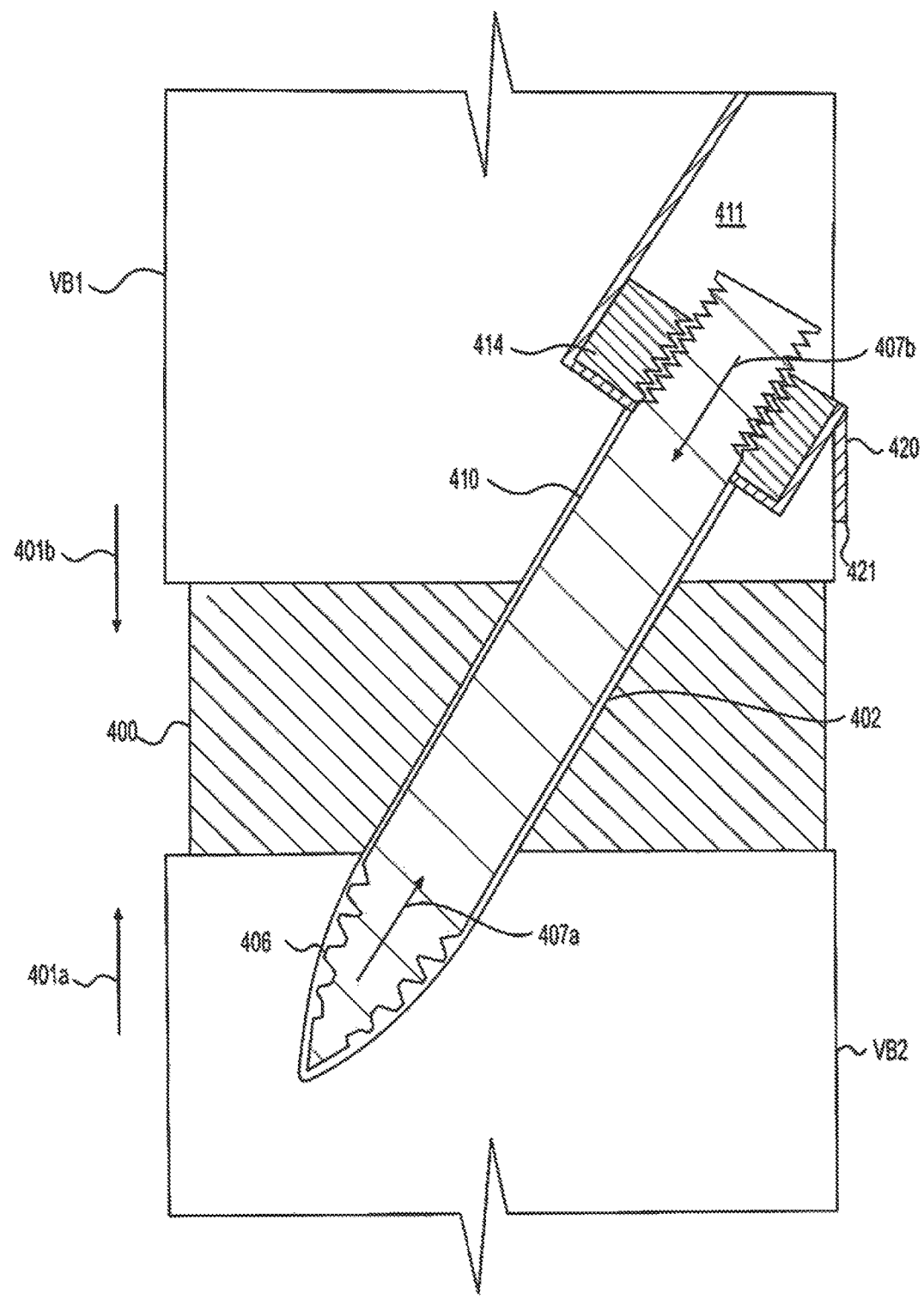
FIG. 4D depicts an apparatus for correcting misalignment of adjacent vertebral bodies, in accordance with a further embodiment of the present disclosure.

As shown in FIG. 4D, e.g., an embodiment of a device for correcting vertebral misalignment may include lining a surface of counterbore 411 with a staple or plate 420. Plate 420 may provide a rigid surface upon which nut 414 may rest. In addition, plate 420 may prevent rotation of nut 414 from further damaging the native structure of the vertebral body. Moreover, plate 420 may assist in preventing nut 414 from disengaging elongate member 410. For example, plate 420 may include a catch (e.g., a projection) (not shown) configured to prevent nut 414 from reversing itself off of elongate member 410. In one embodiment, the catch may include one or more features of the fastener restricting mechanism described above.

Plate 420 may include any suitable configuration. For example, in one embodiment, plate 420 may include a relatively small thickness. In addition, plate 420 may be made of any suitable material. For example, plate 420 may be made of a biocompatible metal, such as, e.g., titanium, stainless steel, nickel, nitinol, or any suitable alloy. In addition, plate 420 may be substantially malleable so as to allow plate 420 to be conformed to an inner surface of counterbore 411. Further, the material of plate 420 may be configured to transition from a substantially flexible (e.g., foil-like) state to a substantially rigid state upon exposure to certain triggers, including, e.g., body chemistry and/or temperature. Further, plate 420 may include a substantially constant thickness, or may include one or more different thicknesses, as shown in, e.g., FIG. 4E.

Plate 420 may be secured to the inside of counterbore 411 by any suitable method known in the art. For example, plate 420 may be adhesively secured to counterbore 411 by, e.g., bone cement. In another embodiment, one or more mechanical fasteners may be used to secure plate 420 to one or more portions of counterbore 411. In some embodiments, a portion 421 of plate 420 may extend out of counterbore 411 and along an external wall of vertebral body VB1, for example. In such embodiments, portion 421 may facilitate anchoring plate 420 to the vertebral body. In addition, portion 421 may prevent damage to weakened portions of the vertebral body structure by, e.g., a tool rotating nut 414. Further, although not shown, additional portions of plate 420 may extend out of counterbore 411 and along any external wall of vertebral body VB1.

Figure 4E:
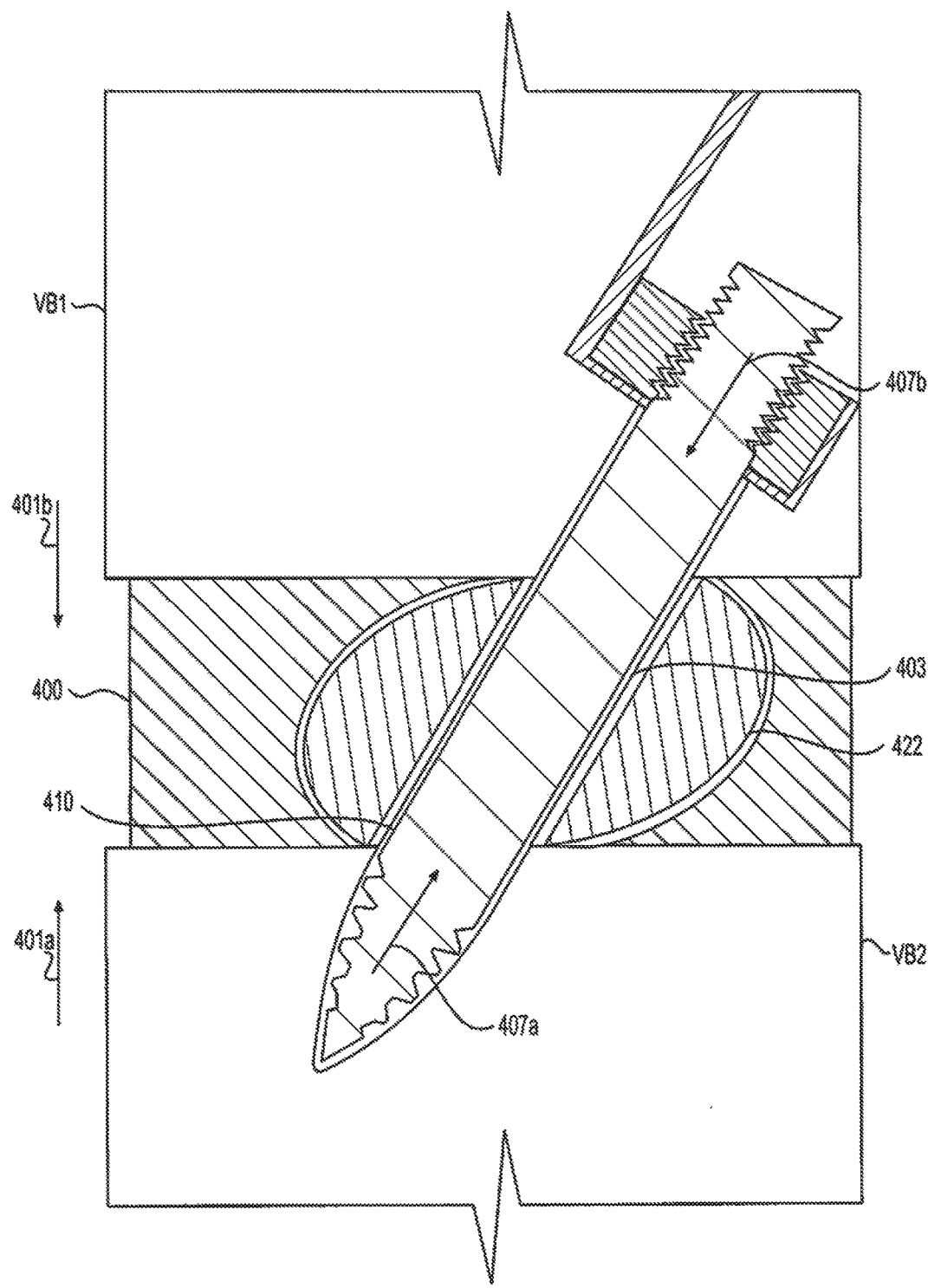
FIG. 4E depicts an apparatus for correcting misalignment of adjacent vertebral bodies, in accordance with another embodiment of the present disclosure.

Turning now to FIG. 4E, there is depicted yet another embodiment of a device for correcting spinal misalignment. The embodiment depicted in FIG. 4E may include one or more of the features described in connection with the other embodiments discussed herein. The embodiment of FIG. 4E includes an adjustable passageway or channel 403. Channel 403 may be made adjustable by any suitable means known in the art. For example, structures may be selectively positioned within or about an opening of channel 403 to alter an angle of channel 403 relative to spacer 400. In the embodiment of FIG. 4E, channel 403 may be formed in an insert 422 that is movable relative to a remainder of spacer 400. Insert 422 may include any suitable configuration known in the art. Insert 422 may include a substantially spherical configuration configured to be movably disposed in an appropriately configured recess in spacer 400. Insert 422 may be made of any suitable material capable of allowing insert 422 to move relative to spacer 400. For example, insert 422 may be made of a plastic configured to minimize friction between insert 422 and spacer 400. In addition, an outer surface of insert 422 and/or an inner surface of the cavity within which it is disposed may include a suitable lubricious coating.

Insert 422 may be manipulated to set an angle of channel 403 through spacer 400 by any suitable means. For example, prior to implanting spacer 400, a physician may manually set a position of insert 422. In another embodiment, insert 422 may be adjusted into position by elongate member 410 as it travels through spacer 400. In an even further embodiment, a suitable tool may be employed to manipulate insert 422 in situ as desired.

Figure 4F:
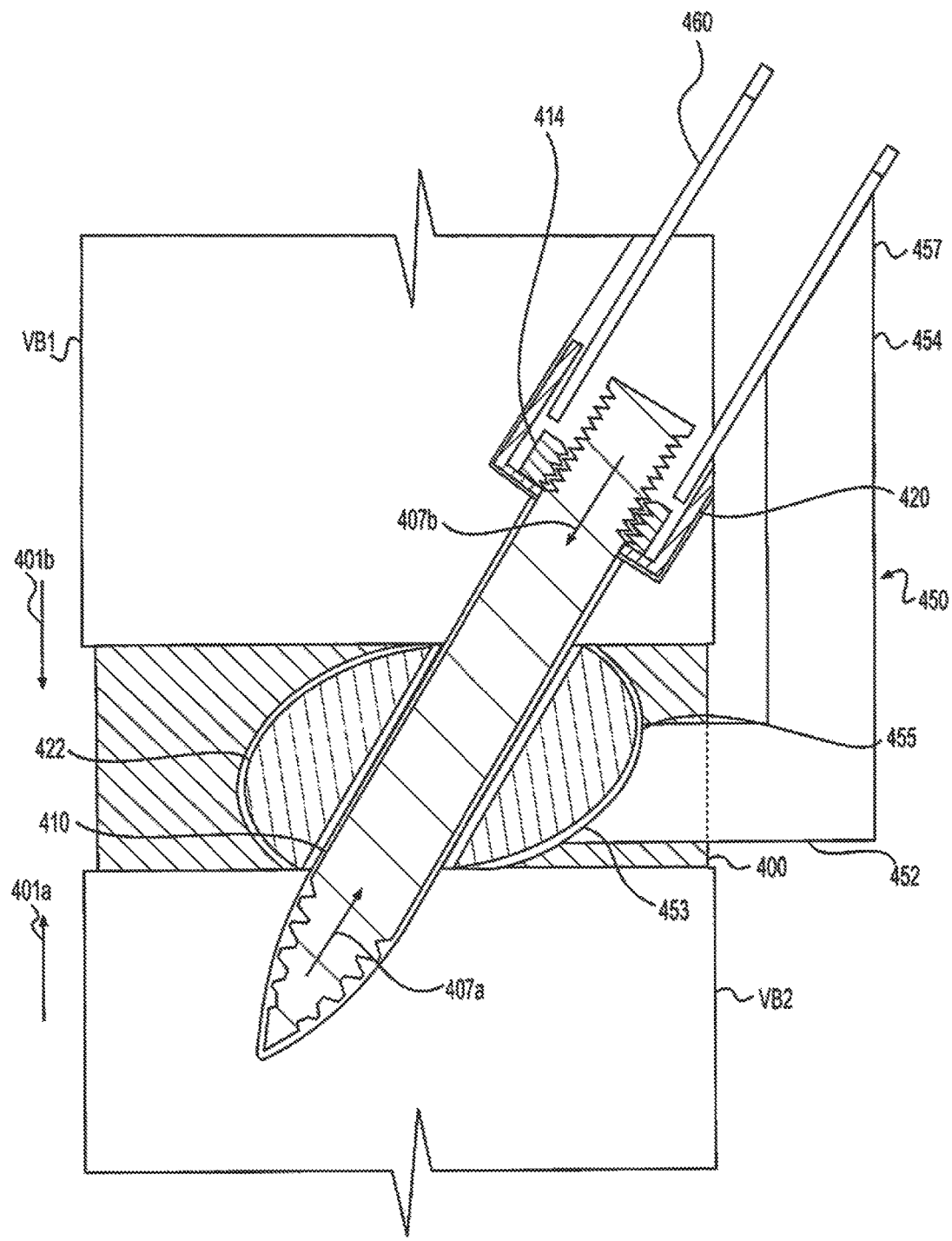
FIG. 4F depicts an apparatus for correcting misalignment of adjacent vertebral bodies, in accordance with yet another embodiment of the present disclosure.

Turning now to FIG. 4F, there is depicted yet another embodiment of a device for correcting vertebral misalignment. The embodiment of FIG. 4F may include one or more features of the embodiment of FIG. 4E. In addition, the embodiment of FIG. 4E may allow for using a tool 450 to, among other things, manipulate insert 422 and guide elongate member 410 therethrough.

As shown in FIG. 4F, tool 450 may include a first portion 452 and a second portion 454. Tool 450 may function as a guide for orienting a cannula 460 for appropriate insertion of elongate member 410. First portion 452 may be integrally formed with second portion 454. In some embodiments, however, first portion 452 may be rigidly connected to second portion 454 by, e.g., welding. An end 453 of first portion 452 opposite to the connection with second portion 454 may be configured follow an angle of insert 422. For example, end 453 may include a curved face 455 having an arc angle corresponding to an outer surface of insert 422. End 453 may include any suitable configuration for following an angle of insert 422. Thus, as insert 422 is manipulated to select a desired angle for channel 403, guide 450 may be accordingly adjusted, thereby setting a corresponding angle for insertion of elongate member 410 via cannula 460. As explained above, end 453 is configured to follow an angle of insert 422. Consequently, first portion 452 and second portion 454 may be adjusted as insert 422 is adjusted. End 457 of second portion 454 may be configured to be removably secured to an insertion cannula 460. Thus, as guide 450 is moved, cannula 460 may be accordingly oriented to correspond to the angle of channel 403.

Figure 5A:
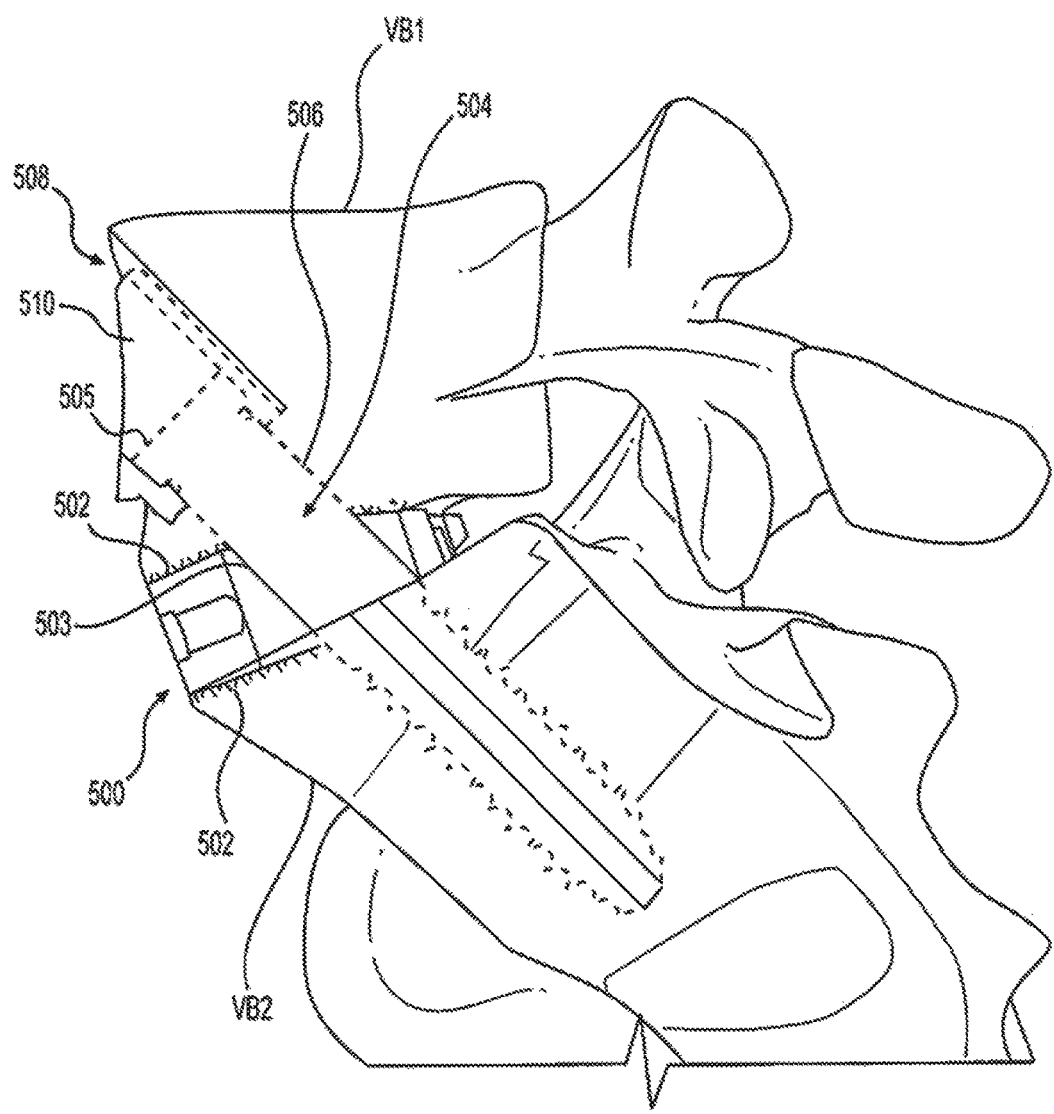
FIGS. 5A-5B depict an embodiment of using an apparatus of the present disclosure to re-position dislocated vertebral bodies.
Figure 5B:
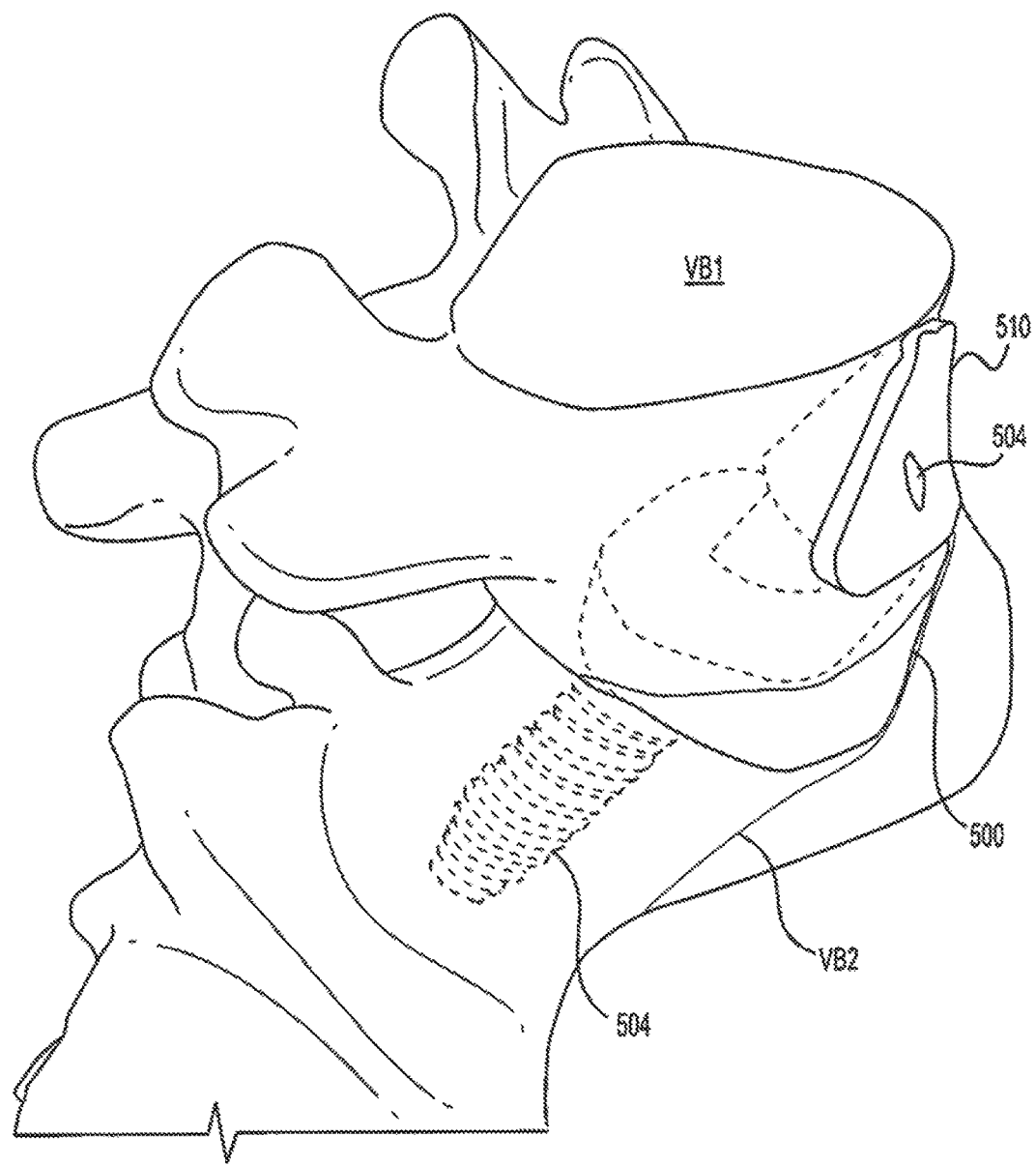

With reference now to FIGS. 5A-5B, a method of using one or more of the embodiments of FIGS. 4A-4F is illustrated and described herein. As noted above, the methods and devices disclosed herein may be used to, among other things, correct misalignment of vertebral bodies, e.g., spondylolisthesis. Although the described method corrects vertebral misalignment via an anterior approach, those of ordinary skill in the art will understand that a posterior approach may be used additionally or alternatively. Further, although the described embodiments discuss moving a superior vertebral body relative to an inferior vertebral body, the inferior vertebral body may be moved additionally or alternatively.

With reference to FIG. 5A, an interbody device 500 is depicted between a superior vertebral body VB1 and an inferior vertebral body VB2. In some cases, the superior vertebral body VB1 may be the L5 vertebral body, and the inferior vertebral body may be the S1 vertebral body. As noted above, however, prior to positioning interbody device between vertebral bodies VB1 and VB2, the native disk may be removed by any suitable procedure. The inferior surface of vertebral body VB1 and the superior body of vertebral body VB2 may be roughened to promote fusion (e.g., ossification) with interbody device 500. To assist with fusion, interbody device 500 may include a plurality of geometric features 502 disposed on one or both of the superior and/or inferior surfaces of interbody device 500. The geometric features 502 may include any suitable configuration and may include barbs, tines, spikes, screws, and the like. In some embodiments, a suitable adhesive (e.g., bone cement) may be used to fixedly connect the interbody device to the adjacent surfaces of one or more of vertebral bodies VB1 and VB2. For example, bone cement may be used to secure interbody device 500 to the superior surface of vertebral body VB2.

The interbody device 500 may include a one-piece construction. In some embodiments, however, the interbody device 500 may include two components fixedly joined together. The components of interbody device 500 may be made of any suitable material including, but not limited to, titanium, stainless steel, PEEK, nickel, or any suitable alloys. Interbody device 500 may further include a channel 503 extending at an angle through interbody device. As well be explained in greater detail below, channel 503 may be configured to receive an elongate member, such as, e.g., a screw 504 therethrough. In some embodiments, an angle at which channel 503 extends through interbody device 500 may be adjustable.

Prior to inserting screw 504, however, a passageway 506 may be created through vertebral body VB1 via a suitable reamer. In some embodiments, a similar passageway may be created in vertebral body VB2 as well. In addition, a counterbore 508 in communication with passageway 506 may be created to receive head 505 of screw 504 therein. The counterbore 508 may be created by any suitable means, including, e.g., reaming. In some embodiments, however, only counterbore 508 may be created. The passageway 506 may be created by screw 504 as it is being driven through vertebral body VB1. Next, a plate 510, which may be similar to plate 420 discussed above, may be disposed in counterbore 508. As shown in FIG. 5A, plate 510 may include a through opening in communication with passageway 506. In addition, as shown in FIG. 5B, portions of plate 510 may extend out of counterbore 508 and adjacent one or more external walls of vertebral body VB1. Next, screw 504 may be advanced through vertebral body VB1, interbody device 500, and into vertebral body VB2. As screw 504 is advanced and tightened, the angle of insertion of screw 504 (resulting from the angle of channel 503) may cause vertebral body VB1 to move posteriorly and inferiorly relative to vertebral body VB2, thereby moving vertebral body VB1 into proper alignment with vertebral body VB2.

Figure 6A:
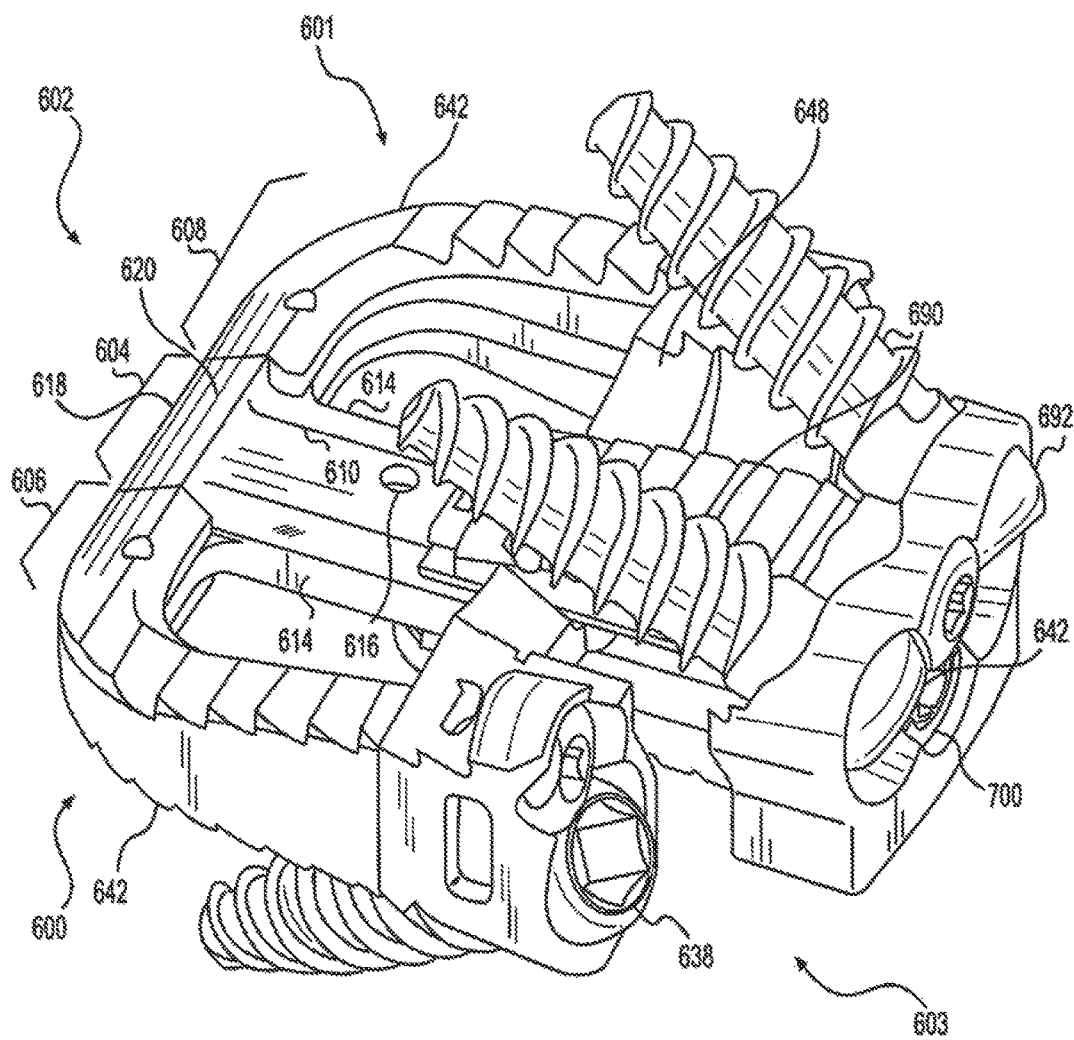
FIG. 6A depicts an apparatus for correcting vertebral misalignment, in accordance with an embodiment of the present disclosure.
Figure 6B:
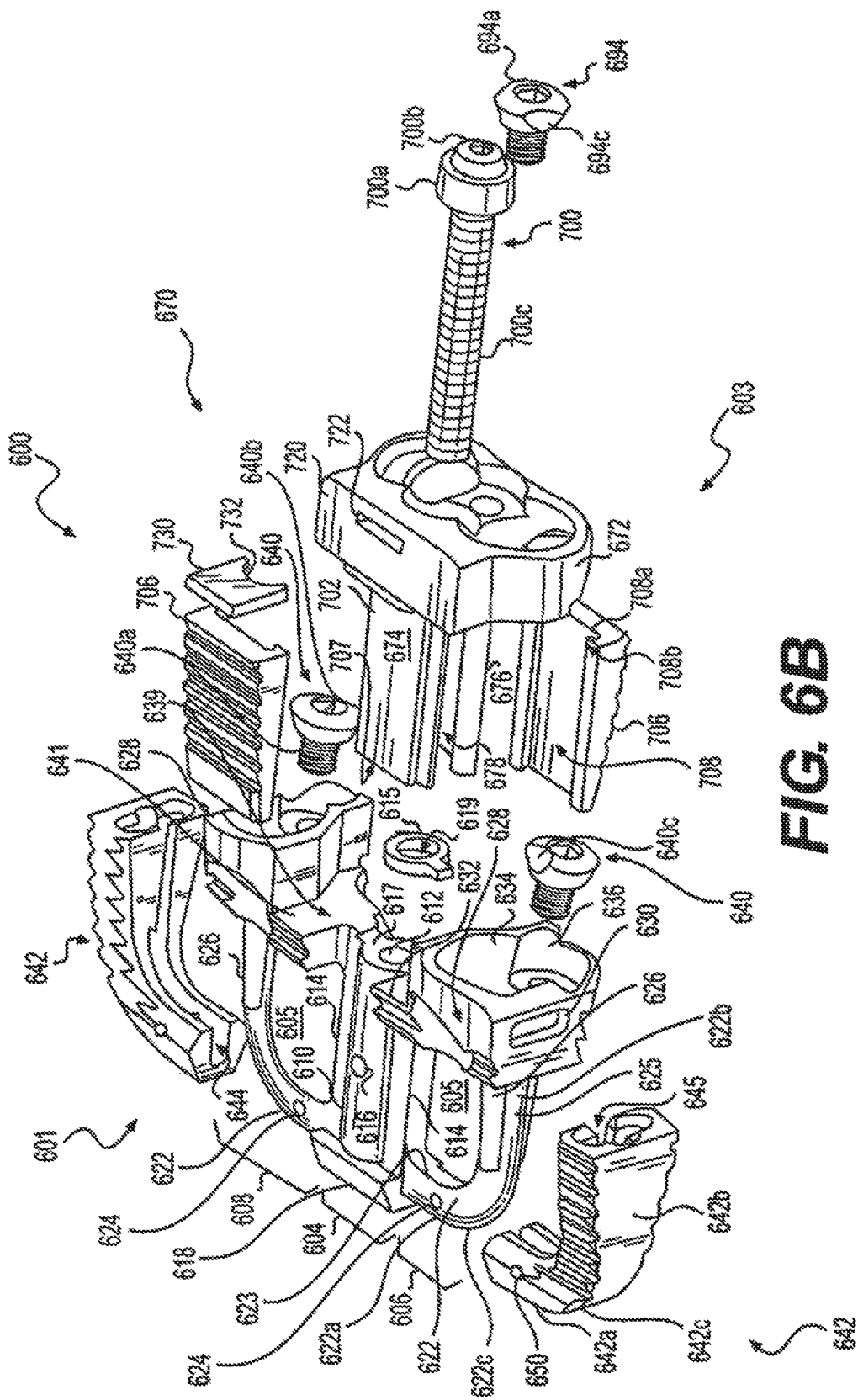
FIG. 6B depicts an exploded view of the apparatus of the FIG. 6A.

Turning now to FIGS. 6A-6B, there is depicted another embodiment of a device assembly 600 for correcting misaligned vertebral bodies, in accordance with the present disclosure. Assembly 600 may include any of the features described in connection with the other embodiments disclosed herein. For example, assembly 600 may include any or all of the features of assembly 10 described above. Assembly 600 includes a frame member 602. Frame member 602 may include any suitable configuration for disposal in the interbody disk space between two adjacent vertebral bodies, such as, e.g., the L5 and S1 vertebral bodies. Of course, frame member 602 may be configured for disposal between any other two adjacent vertebral bodies.

Frame member 602 includes a posterior end 601 and an anterior end 603. In addition, frame member 602 includes a central section 604, a right lateral section 606, and a left lateral section 608. The "right" and "left" designations are assigned when assembly 600 is oriented and disposed in the interbody disk space between two adjacent vertebral bodies, for example.

Central section 604 includes a longitudinal member 610 defining a lumen 612 therethrough. Lumen 612 may be in communication with an opening disposed in an anterior end face 617 of longitudinal member 610. The anterior end face 617 may be configured to receive a friction ring 615 thereon, which will be described in greater detail below. In the depicted embodiment, longitudinal member 610 may include a substantially cylindrical configuration having flanges 614 extending laterally away therefrom. Those of ordinary skill will understand that longitudinal member 610 may not be limited to a cylindrical configuration. In fact, longitudinal member 610 may include any suitable configuration known in the art. Lumen 612 may be a substantially circular lumen configured, e.g., to receive a suitable fastener therein. However, lumen 612 may include any suitable configuration. Lumen 612 may extend an entire length of longitudinal member 610. In some embodiments, however, lumen 612 may only extend along a portion of longitudinal member 610. In some embodiments, lumen 612 may include suitable geometric features therein for interacting and retaining a fastener received therein. In one embodiment, the geometric features may include internal screw threads. Further, as can be seen in FIGS. 6A-7B, longitudinal member 610 may include a through hole 616 extending from a superior external surface of longitudinal member 610 through lumen 612 and to an inferior external surface of longitudinal member 610. Through hole 616 is utilized in the peening process for the central actuator or longitudinal member 610. Once the longitudinal member 610 is threaded into through hole 698, a portion of the male threads are deformed via through hole 616 thereby preventing the back out of the longitudinal member from the inner member. Further, both longitudinal member 610 and lumen 612 may include substantially constant cross-sectional diameters. However, those of ordinary skill in the art will understand that the diameters of either longitudinal member 610 or lumen 612 may vary along the lengths thereof. For example, the diameters of one or both of longitudinal member 610 and lumen 612 may reduce when moving posteriorly from anterior end 603.

Flanges 614 may be disposed adjacent a central longitudinal axis of lumen 612. As shown in FIG. 6A, e.g., the transition from the substantially cylindrical outer surface of longitudinal member 610 to flanges 614 may be substantially smooth. In addition, each of flanges 614 may be integrally formed with longitudinal member 610. However, in some embodiments, flanges 614 may be secured to longitudinal member 610 by, e.g., welding. Flanges 614 may include a generally rectangular cross-sectional configuration. However, one or both of flanges 614 may include any suitable configuration. In addition, the configuration of flanges 614 may not be identical to one another. For example, a left flange 614 may include a rectangular cross-sectional configuration, while the right flange may include a trapezoidal configuration (not shown).

Central section 604 may further include a posterior portion 618. Posterior portion 618 may extend posteriorly from longitudinal member 610. In addition, posterior portion 618 may extend farther in the superior direction than both of flanges 614 and longitudinal member 610. Posterior portion 618 may also extend farther in the inferior direction than both of flanges 614 and longitudinal member 610. Further, one or both of anterior surface 620 and inferior surface (not shown) of posterior portion 618 may be slanted to provide posterior portion 618 with a tapered configuration. Still further, a posterior surface (not shown) of posterior portion 618 may be substantially planar.

Central section 604 may be integrally formed with one or both of right lateral section 606 and left lateral section 608. However, in some embodiments, the right and left lateral sections 606, 608 may be secured to central section 604 by any suitable means known in the art, including, e.g., welding.

With reference primarily to FIG. 6B, the right and left lateral sections 606, 608 may include substantially similar features. Indeed, the right and left lateral sections 606, 608 may be effectively mirror images of one another. For the purposes of efficiency, therefore, only right lateral section 606 will be described herein. However, those of ordinary skill in the art will understand that the right and left lateral sections 606, 608 also may include differing configurations (not shown).

Originating from approximately the location of the interface between posterior portion 618 and longitudinal member 610/flanges 614, an extension member 622 may extend laterally away from central section 604. As shown in FIG. 6B, extension member 622 may first extend laterally away from central section 604 and then curve to extend in the anterior direction. That is, extension member 622 may include a first portion 622*a* extending substantially perpendicularly to longitudinal member 610, and a second portion 622*b* extending substantially parallel to central section 604. First and second portions 622*a* and 622*b* may be connected by a central portion 622*c*. Central portion 622*c* may be curved, as shown in FIG. 6B. However, central portion 622*c* may be effectively eliminated and first and second portions 622*a* and 622*b* may be joined by a right angle elbow (not shown). As can be seen in FIG. 6B, e.g., extension member 622 and longitudinal member 610 may define a plurality of through openings 605 therebetween. The openings 605 may be configured to receive bone cement therein during an implantation procedure.

Extension member 622 may include a substantially planar internal surface 623. In addition, extension member 622 may include a curved external surface 625. However, those of ordinary skill will understand that any suitable configuration may be employed for internal and external surfaces 623, 625. Further, extension member 622 may include substantially planar superior and inferior surfaces. However, in some embodiments, the superior and inferior surfaces of extension member 622 may include suitable geometric configurations for receiving and retaining an endplate, as discussed in greater detail below. As shown in FIG. 6B, first portion 622*a* may include a hole 624 for facilitating retention of the aforementioned endplate. Hole 624 may include suitable geometric configurations for retaining a fastener therein. In one embodiment, hole 624 may include internal threads (not shown) configured to cooperate with a screw (not shown).

Second portion 622*b* of extension member 622 may include one or more geometric features to assist with retaining the aforementioned endplates. In one embodiment, one or both of the superior and/or inferior surfaces of second portion 622*b* may include a rib 626. Rib 626 may include any suitable configuration known in the art. For example, rib 626 may include a rounded projection extending away from the respecting superior/inferior surfaces. In some embodiments, rib 626 may include a length along a substantial portion of second portion 622*b*. However, rib 626 may not necessarily extend the full length of second portion 622.

An anterior end portion of extension member 622 may be integrally formed with an enlarged head portion 628. Head portion 628 may include any of the features described above in connection with head portions 42, 42*a*. For example, in one embodiment, a lateral face of each portion 628 may include a geometric feature 630 substantially similar to geometric feature 64 described above. In particular, geometric feature 630 may include a notch for allowing a tool (not shown) to grip and manipulate assembly 600. Further, superior and inferior surfaces of head portion 628 may include one or more geometric features 632 configured to increase friction between assembly 600 and adjacent bony surfaces. The geometric features 632 may include a plurality of pyramid-like projections and corresponding valleys. In other embodiments, the superior and/or inferior surfaces may include, but are not limited to, barbs, tines, hooks, etc. In addition, or alternatively, the superior and/or inferior surfaces may include a suitable porous structure configured to promote bone ingrowth. Further, the superior and/or inferior surfaces may include a coating for promoting bone ingrowth. In one embodiment, the coating may include hydroxyapatite. Of course, any portion of assembly 600 may include any suitable coating, including, but not limited to, coatings containing therapeutic, antibiotic, and/or anesthetic agents.

The anterior surface of head portion 628 may define at least two counterbores 634, 636. Counterbore 634 may be in communication with a coaxial hole extending through head portion 628 at an angle relative to a longitudinal axis (not shown) of central section 604 (e.g., longitudinal member 610). Counterbore 634 may be substantially spherical, and configured to receive a spherical head of a fastener (described below in greater detail) therein. In one embodiment, counterbore 634 and its associated coaxial hole may be configured to guide the received fastener at an angle in the inferior direction away from frame member 602. In addition, the counterbore 634 and its associated coaxial hole may be configured to guide the received fastener toward a central vertical axis (not shown) of frame member 602. Thus, the fasteners received in the two depicted head portions 628 may be disposed in a converging relationship relative to one another. As described below, the fasteners received in head portions 628 may include suitable bone screws 638.

Counterbore 636 may be relatively smaller in diameter than counterbore 634. In addition, counterbore 636 may be in communication with a blind coaxial hole (not shown). Counterbore 636 may be configured to receive therein a set screw 640 including a threaded portion 640*a* and a head portion 640*b*. Head portion 640*b* may be configured to include a cam-style blocking mechanism, as described above. Indeed, set screw 640 may be substantially similar to fastener restricting mechanism 72. More particularly, head portion 640*b* may include a cut-out portion 640*c* configured to allow bone screw 638 to pass by set screw 640 when cut-out portion 640*c* is disposed in the travel path of bone screw 638. However, if set screw 640 is rotated to move cut-out portion 640*c* out of the travel path of bone screw 638, a portion of head portion 640*b* may abut a head of bone screw 638, thereby restricting its longitudinal movement. Those of ordinary skill will readily understand that any suitable mechanism for preventing bone screw 638 from reversing itself out of engagement may be utilized in accordance with the principles of the present disclosure.

Head portions 628 may be connected to an anterior end of central section 604 via central connections 639. Central connections 639 may include any suitable configuration for supporting head portions 638. For example, central connections 639 may include substantially planar anterior surfaces 641, which may or may not be disposed flush with anterior surface 617. Indeed, in some instances, anterior surfaces 641 may be raised (by, e.g., a dimension corresponding to a thickness of friction ring 615) relative to anterior surface 617 to provide a seat for friction ring 615. Further, the inferior 646 surfaces of central connections 639 may include suitable geometric configurations for increasing friction relative to an adjacent bony surface, as described herein. With reference to FIG. 6B, anterior surfaces 617, anterior surfaces 641, and lateral surfaces of head portions 628 may define a cavity dimensioned for receiving an anterior head portion 672 of a reducing plate 670 therein, as described in greater detail below.

With continuing reference to FIG. 6B, each extension member 622 may be configured to receive an end plate 642 thereon. End plate 642 may include any suitable configuration for being disposed about extension member 622. End plate 642 may include a first portion 642a, a second portion 642b, and a third portion 642c connecting the first and second portions 642a, 642b. First, second, and third portions 642a, 642b, and 642c may be formed integrally with one another. In other embodiments, however, first, second, and third portions 642a, 642b, and 642c may be fixedly secured to one another by any suitable means known in the art.

First portion 642a may be configured to be received on first portion 622a of extension portion 622. Accordingly, first portion 642a may include an internal channel 644 having internal geometry corresponding to an external geometry of first portion 622a. The channel 644 may be configured to extend from a first terminal end face of end plate 642 to a second terminal end face of end plate 642. In addition, channel 644 may be configured to receive extension member 622 therein via an opening 645 in an external wall of end plate 642. Like channel 644, opening 645 also may be configured to extend from a first terminal end face of end plate 642 to a second terminal end face of end plate 642. In one embodiment, end plate 642 may be substantially flexible such that it may open in a clam-like manner, thereby enlarging opening 645 so that extension member 622, and rib 626, may be received in channel 644. Further, a depth of channel 644 and opening 645 may be dimensioned such that when end plate 642 is disposed about extension member 622, the respective surfaces of end plate 642 disposed above and below opening 645 are flush with surface 623 of extension member 622.

First portion 642a may be dimensioned such that its superior and inferior surfaces are flush with respective surfaces of posterior portion 618. For example, the superior and inferior surfaces of first portion 642a may include a slant or taper similar to the slant/taper of surface 620. First portion 642a may also include a hole 650 configured to receive a fastener (e.g., a set screw) for fixedly securing end plate 642 to extension member 622.

Like first portion 642a, second and third portions 642b, 642c may be configured to be disposed about second and third portions 622b, 622c of extension member 622. As explained above, channel 644 may include a suitable internal geometry for cooperating with an external geometry of extension member 622. Thus, the portion of channel 644 in second portion 642b may include cutouts for accommodating one or more rib(s) 626. In addition, as shown in FIGS. 6A-6B, end plate 642 may be configured to progressively increase in height from a posterior portion to an anterior portion, such that its anterior end may be substantially similar to a posterior end face of head portion 628. Further, the superior and inferior surfaces of end plate 642 may include any suitable geometric configurations (e.g., rows of directional teeth, barbs, pyramids, etc.) configured to increase friction between end plate 642 and an adjacent bony surface.

End plate 642 may be fabricated via any suitable method known in the art. For example, end plate 642 may be molded or extruded. In addition, end plate 642 may be made of any suitable material. In one embodiment, end plate 642 may be made of a suitable organic polymer thermoplastic, such as, e.g., PEEK. In addition, one or more surfaces of end plate 642 may be configured to promote bone ingrowth. For example, superior and/or inferior surfaces of end plate 642 may include a porous structure to facilitate tissue infiltration. In addition, surfaces of end plate 642 may include any suitable coating, including, but not limited to, hydroxyapatite and/or coatings containing therapeutic, antibiotic, and/or antiseptic agents.

Figure 6C:
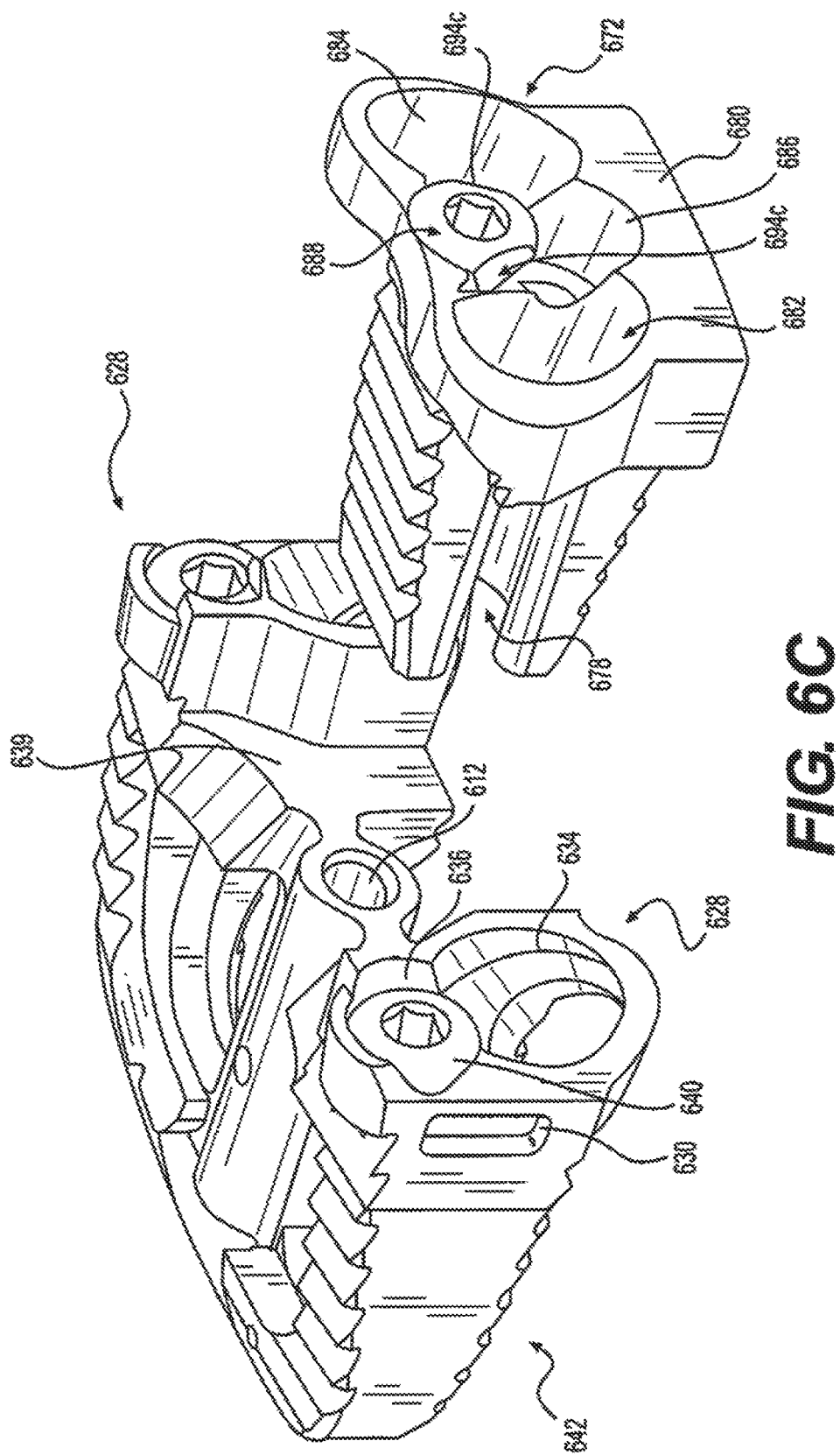
FIG. 6C depicts a partially assembled view of the subcomponents of the apparatus of FIG. 6A.

With continuing reference to FIGS. 6B and 6C, e.g., assembly 600 may further include a reducing plate 670. Reducing plate 670 may include an anterior head portion 672. Anterior head portion 672 may include any suitable configuration. For example, anterior head portion 672 may be dimensioned to be received in the cavity defined by anterior surfaces 617, anterior surfaces 641, and lateral surfaces of head portions 628 described above, such that an anterior-most surface of reducing plate 670 may be substantially flush with respective surfaces of head portions 628 when reducing plate 670 is received in the aforementioned cavity.

Reducing plate 670 may define a mechanism for being received slidingly on longitudinal member 610. For example, in one embodiment, reducing plate 670 may include a plurality of extension plates extending posteriorly from a posterior surface of anterior head portion 672. The plurality of plates may include an inferior extension plate 674 and a superior extension plate 676. Although only two extension plates 674, 676 are depicted, those of ordinary skill in the art will understand that any suitable number of extension plates 674, 676 may be provided. Extension plates 674, 676 may be spaced from one another to define a channel 678 therebetween. In some embodiments, channel 678 may be a closed channel (not shown). In such embodiments, lateral edges of extension plates 674, 676 may be joined together by, e.g., a wall (not shown). However, in the depicted embodiment, channel 678 is depicted as a channel having open side walls. The channel 678 may include a geometry corresponding to an outer geometry of longitudinal member 610 and flanges 614 so that reducing plate 670 may be slidably received on longitudinal member 610, as shown in FIG. 6A. In addition, extension plates 674, 676 may include a length such that posterior-most surfaces of extension plates 674, 676 abut anterior surfaces of posterior portion 618 when anterior head portion 672 is fully received within the cavity defined by anterior surfaces 617, anterior surfaces 641, and lateral surfaces of head portions 628 described above.

The inferior surface 702 of inferior extension plate 674 may be configured to receive an end plate 706 thereon. Accordingly, surface 702 may include one or more geometric features configured to retain end plate 704 on surface 702. In one embodiment, end plate 704 may be slid onto surface 702. Accordingly, surface 704 may include a central raised portion 707 flanked by a stepped portion on either side. The central raised portion may define a rail along which end plate 704 may slide. The superior surface (not shown) of superior extension plate 676 may include features similar to those of surface 702.

End plates 706 may be configured to be received on extension plates 674, 676. End plates 706 may include any suitable configuration. Further, the configuration of each end plate 706 may be substantially similar. Accordingly, for the purposes of efficiency, only one end plate 706 will be described hereafter. In one embodiment, end plate 706 may be formed of a one-piece construction by, e.g., molding or extrusion. Further, end plate 706 may be formed of any suitable material, including, e.g., a suitable organic polymer thermoplastic, such as, e.g., PEEK. In addition, end plate 706 may include a generally tapering configuration. That is, as shown in FIG. 6B, a thickness of a posterior portion of end plate 706 may be smaller than a thickness of an anterior portion of end plate 706. An outer side of end plate 706 may include a plurality of suitable geometric features configured to increase friction between end plate 706 and adjacent bony surfaces. The geometric features may include, e.g., projections, teeth, barbs, tines, spikes, and the like. For example, as shown in FIG. 6B, end plate 706 may include a plurality of rows of teeth.

An inner side of end plate 706 may define a groove 708 for being disposed about central portion 707, so that end plate 706 may be received thereon. Accordingly, groove 708 may be appropriately dimensioned and configured. In one embodiment, groove 708 may include a substantially T-shaped configuration. That is, as shown in FIG. 6B, e.g., sides of groove 708 may extend into side walls of end plate 706 to define a portion of groove 708 being covered by overhang 708b. Further, overhang 708b may be configured to be received in appropriately configured recesses on either side of central portion 707 so as to frictionally retain end plate 706 on extension members 674, 676.

An anterior-most surface 680 of anterior head portion 672 may include a plurality of counterbores therein. For example, as shown in FIG. 6C, surface 680 may include four counterbores 682, 684, 686, and 688, each of which may be in communication with one another. Counterbores 682 and 684 may be substantially similar to each other and therefore will be described together.

Counterbores 682 and 684 may be in communication with respective coaxial holes (not shown) extending through anterior head portion 672. Counterbores 682 and 684 and/or their respective coaxial holes may include suitable geometric features (e.g., internal screw threads) for retaining a suitable fastener (e.g., a bone screw 690) therein. Counterbores 682 and 684 may be substantially spherical in configuration so as to at least partially accommodate spherical heads 692 of bone screws 690. Those of ordinary skill in the art will understand that any suitable fasteners may be used in place of bone screws 690. In one embodiment, counterbores 682, 684 and their respective coaxial holes may be configured to guide bone screws 690 received therein in a superior direction at an angle relative to a longitudinal axis (not shown) of lumen 612. In addition, counterbores 682, 684 and their respective coaxial holes may be configured to guide bone screws 690 received therein away from a central vertical axis (not shown) of frame member 602. Thus, the fasteners received in counterbores 682 and 684 may be disposed in a diverging relationship relative to one another. In other embodiments, the fasteners may be disposed in a converging relationship relative to one another.

Figure 7A:
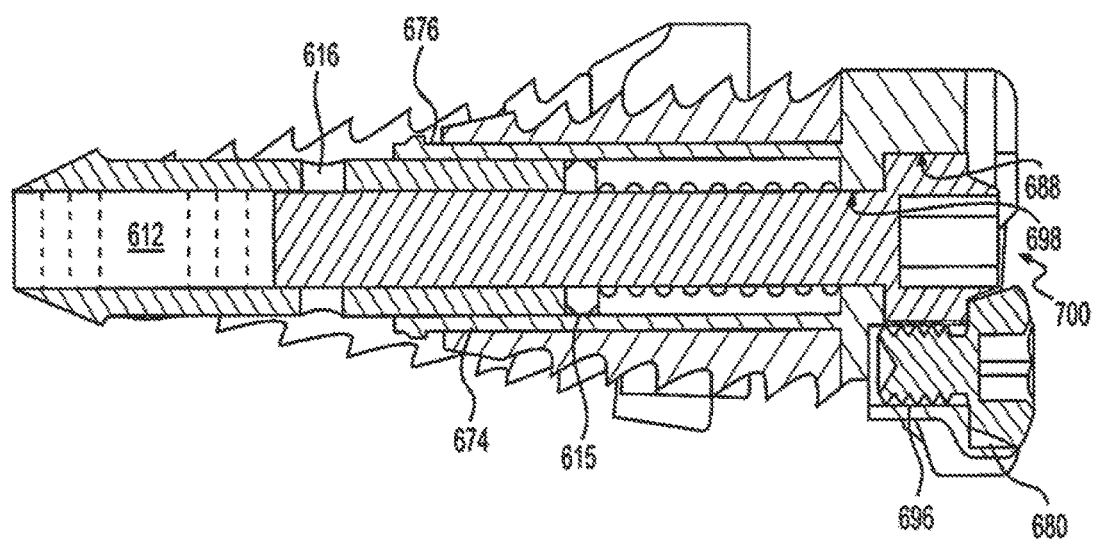
FIGS. 7A-7B depict sagittal cross-sectional views of the apparatus of FIG. 6A in expanded and contracted configurations, respectively.
Figure 7B:
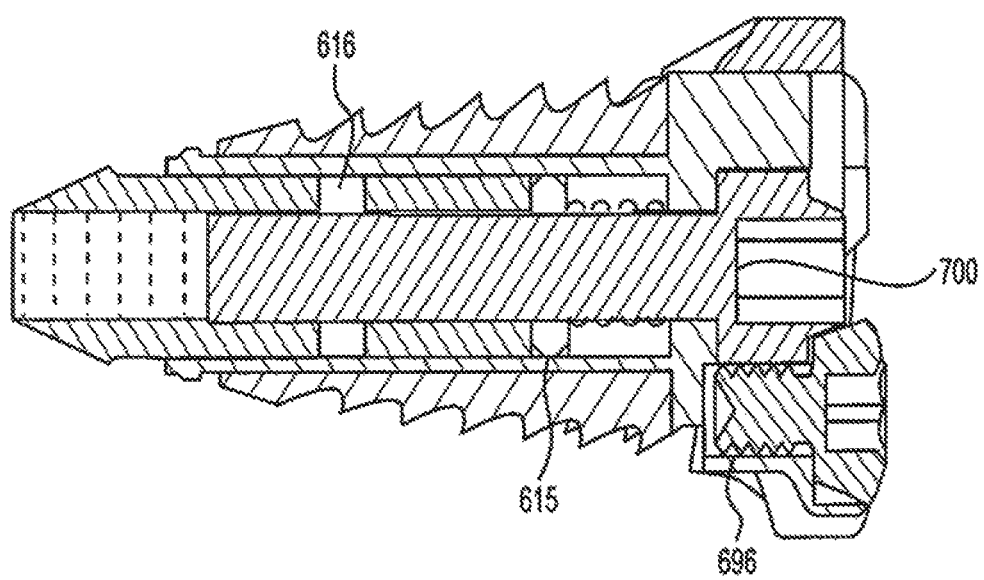

Counterbore 686 may be in communication with a coaxial through hole 698 (shown in FIGS. 7A-7B). When reducing plate 670 is received over longitudinal member 610, counterbore 688 and hole 698 may be in communication with lumen 612 for collectively receiving actuator 700 therein. One or both of counterbore 686 and through hole 698 may include geometric features (e.g., internal screw threads) for retaining actuator 700 therein. Further, as shown in FIG. 6A, counterbore 686 may be dimensioned to completely receive a head 700a of actuator 700. As will be described in greater detail below, actuator 700 may be used to position reducing plate 670 relative to frame member 602, so as to correct vertebral misalignment.

Counterbore 688 may be in communication with a coaxial blind hole 696 (shown in FIGS. 7A-7B) for receiving a set screw 694 incorporating a plurality of the cam-style blocking mechanisms described above. The coaxial blind hole 696 may include suitable geometric features (e.g., internal screw threads) for retaining set screw 694 therein. Those of ordinary skill will readily understand that instead of set screw 694, any suitable fastener restricting mechanism may be used in accordance with the principles of the present disclosure. Set screw 694 may include any of the features of fastening restricting mechanism 72 described above. Further, it is contemplated that set screw 694 may be configured to simultaneously restrict one or more of bone screws 690 and actuator 700 (discussed below in greater detail) from longitudinal travel. For example, in one embodiment, a head 694a of screw 694 may include a plurality of cutouts 694c. As explained above, cutouts 694c may allow the heads of screws 690 and/or actuator 700 to pass head 694a of screw 694 when the cutouts 694c are positioned in the path of travel of screws 690 and/or actuator 700, respectively. However, when cutouts 694c are moved out of the path of travel of screws 690 and/or actuator 700, a portion of head 694a may interfere with the heads of screws 690 and/or actuator 700, thereby restricting their longitudinal movement. Cutouts 694c may be moved into and out of the travel paths by rotating screw 694 within hole 696 via, e.g., any suitable tool known in the art.

Actuator 700 may be any suitable actuator known in the art. For example, actuator 700 may be a threaded bolt or screw including a head 700a having an opening 700b therein for allowing a tool to selectively rotate actuator 700. Actuator 700 may also include a shaft 700c extending away from head 700a from a side of head 700a opposite to opening 700b. The shaft 700c may include suitable geometric features (e.g., internal screw threads) for retaining actuator 700 in, e.g., lumen 612. As shown in FIGS. 7A-7B, actuator head 700a may be received in counterbore 688. In addition, shaft 700c may be received through hole 798 so that it may extend between extension plates 674, 676, through an opening 619 in friction ring 615 and into lumen 612.

Friction ring 615 may include any suitable structure configured to threadingly receive shaft 700c of actuator 700. In some embodiments, friction ring 615 may be made of a suitable organic polymer thermoplastic, such as, e.g., PEEK. Friction ring 615 may be formed by any suitable process known in the art, including, e.g., molding, machining, or extrusion. As noted above, friction ring 615 may include an opening 619 corresponding to lumen 612. In addition, friction ring 615 may be configured to be disposed adjacent surface 617 of longitudinal member 610. In one embodiment, friction ring 615 may be made integrally with surface 617. In another embodiment, friction ring 615 may be secured to surface 617 by, e.g., a suitable adhesive.

With reference now to FIG. 6B, an inferior surface 720 of anterior head portion may include an opening 722 in communication with a slot. The slot may be in communication with counterbore 688. In one embodiment, opening 722 may be configured to receive therein a blocking plate 730. Blocking plate 730 may include a substantially square or rectangular configuration. However, one side of blocking plate 730 may include a geometric feature 732 configured to surround and engage head 700a of actuator 700. Geometric feature 732 may be configured to engage head 700a in the manner a wrench may engage the head of a nut, as will be appreciated by those of ordinary skill in the art. Blocking plate 730 may be made of any suitable material known in the art, including, but not limited to, titanium, stainless steel, nickel, and/or any suitable alloys. Further, blocking plate 730 may be dimensioned such that when geometric feature 732 engages with head 700a, blocking plate 730 is received completely within opening 722. Further, blocking plate 730 may be secured within opening 722 and its associated slot by any means known in the art. For example, a suitable adhesive (not shown) may be used to fix blocking plate 730 into opening 722.

Furthermore, portions of assembly 600 may be radiolucent or radiopaque as desired. In addition, assembly 600 may include any suitable radiopaque markings necessary to assist with visualizing assembly 600 within a patient's body.

Assembly 600 may be used to correct misalignment of adjacent vertebral bodies (e.g., the L5 and S1 vertebral bodies), including, but not limited to, spondylolisthesis. Assembly 600 may be pre-assembled with reducing plate 670 thereon prior to implantation. Prior to implanting assembly 600 within a patient, however, a patient's native disc may be first removed by, e.g., a discectomy procedure. Next, the surfaces of the vertebral body immediately adjacent the interbody disk space may be roughened, as is known in the art. Subsequently, frame member 602 may be positioned in the interbody disk space. Prior to positioning frame member 602, however, a physician or other healthcare provider may manually manipulate the dislocated vertebral bodies into proper alignment so as to identify an appropriate positioning of frame member 602 relative to, e.g., an inferior vertebral body. Once appropriately positioned, screws 640 may be rotated so that cutouts 640c are positioned in the path of travel of bone screws 638, and bone screws 638 may be inserted into counterbores 634 to fasten frame member 602 to an inferior vertebral body. Screws 640 may be once again rotated to move cutouts 640c out of the path of travel of screws 638, so that a remaining portion of a head of screw 640 may engage the heads of screw 638 to retain them in position.

Next, screw 694 may be manipulated to dispose cutouts 694c in the path of travel of bone screws 690. Subsequently, bone screws 694 may be advanced into counterbores 682 and 684 and into a superior vertebral body to secure reducing plate 670 to the superior vertebral body. Then, screw 694 may be manipulated to move cutouts 694c out of the path of travel of screws 690, so that a remaining portion of head 694a may engage the heads 692 of screws 690 to retain them in position. Head 694a may also function to restrict longitudinal movement of actuator 700.

Subsequently, in some embodiments, bone cement may be disposed in openings 605, as desired. Next, any displacement between the superior and inferior vertebral bodies may be corrected by gradually turning actuator 700 to move reducing plate 670 in the posterior direction over longitudinal member 610. Once the desired amount of correction is achieved, actuator 700 may be fixed in place so that a position of reducing plate 670 is fixed relative to frame member 602. Actuator 700 may be fixed in place my manipulating screw 694 so that, in addition to restricting movement of screws 690, screw 694 also restricts further movement of actuator 700. Further, blocking plate 730 may be inserted into and secured (via, e.g., an adhesive) within opening 722, such that feature 732 engages actuator head 700a and prevents it from rotating. Any cement inserted into openings 605 may be allowed to cured and the procedure may be completed as customary in the art.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A method of correcting vertebral misalignment, the method comprising:
    positioning an implant within a space between two adjacent vertebral bodies, wherein the implant comprises:
        a frame assembly having a posterior end and an anterior end, the frame includes a central section, a right lateral section, and left lateral section, the central section includes a longitudinal member having a lumen, the longitudinal member extends from the posterior end to the anterior end of the frame;
        a reducing plate configured to be slidably received over the longitudinal member, wherein the reducing plate is configured to be secured to a second vertebral body; and
        an actuator configured to extend through an opening in the reducing plate and into the lumen of the longitudinal member, the actuator configured to move the reducing plate relative to the frame,
        wherein the central section, the right lateral section and the left lateral section are integrally formed,
        wherein the assembly includes a first endplate and a second endplate, the first endplate coupled to the left lateral section of the frame and the second endplate coupled to the right lateral section of the frame, wherein the frame includes an enlarged head portion configured to receive a fastener for securing the assembly to the first vertebral body, wherein the enlarged head portion is further configured to receive a fastener restricting mechanism for limiting longitudinal travel of the fastener; and
    securing the frame assembly to a first vertebral body of the two adjacent vertebral bodies;
    securing the reducing plate to a second vertebral body of the two adjacent vertebral bodies, wherein the second vertebral body is disposed superiorly of the first vertebral body;
    rotating the actuator to move the second vertebral body relative to the first vertebral body; and
    securing the reducing plate relative to the frame assembly.

2. The method of claim 1, further comprising one of removing a native disc prior to positioning the implant or roughening a vertebral body surface adjacent the space.

3. The method of claim 1, wherein the first vertebral body is the L5 vertebral body.

4. The method of claim 3, wherein the second vertebral body is the S1 vertebral body.

5. The method of claim 1, further comprising securing the frame assembly to the space with bone cement.

6. The method of claim 1, wherein securing the frame assembly to the first vertebral body includes advancing a plurality of threaded fasteners through the frame assembly and into the first vertebral body.

7. The method of claim 6, wherein the plurality of threaded fasteners are advanced into the first vertebral body in directions towards one another.

8. The method of claim 6, further comprising providing a fastener restricting mechanism and activating the fastener restricting mechanism to retain at least one of the plurality of threaded fasteners relative to the frame assembly.

9. The method of claim 1, wherein securing the reducing plate to the second vertebral body includes advancing a plurality of threaded fasteners through the reducing member and into the second vertebral body.

10. The method of claim 9, further comprising providing a fastener restricting mechanism and activating the fastener restricting mechanism to retain at least one of the plurality of threaded fasteners relative to the reducing member.

11. The method of claim 9, wherein the plurality of threaded fasteners are advanced through the reducing plate in directions away from one another.

12. The method of claim 10, wherein securing the reducing plate relative to the frame assembly includes preventing rotating of the actuator.

13. The method of claim 12, wherein the fastener restricting mechanism prevents rotation of the actuator.

14. A method of correcting vertebral misalignment, the method comprising:
 accessing adjacent vertebral bodies via an anterior-only approach;
 removing a native disc from in between the adjacent vertebral bodies to form an interbody disc space;
 roughening one or more surfaces of one or both of the adjacent vertebral bodies;
 positioning an implantable assembly within the interbody disc space, wherein the implantable assembly comprises:
  a frame assembly including a left lateral portion, a central portion, and a right lateral portion, wherein the left and right lateral portions define enlarged heads configured to receive fasteners therein for securing the frame assembly to a first vertebral body, and wherein the central portion includes a longitudinal member extending from a posterior end to an anterior end of the frame, the longitudinal member having a lumen therethrough;
  a reducing member configured to be slidably received over the longitudinal member, wherein the reducing member includes an anterior portion and a plurality of extensions extending posteriorly therefrom, wherein the plurality of extensions define a channel therebetween, wherein the channel is configured to receive a portion of the frame;
  an actuator configured to extend from an anterior surface of the reducing member into the lumen of the longitudinal member of the frame assembly, the actuator configured to control a position of the reducing member relative to the frame assembly; and
  a plurality of fastener restricting mechanisms for retaining the fasteners within the enlarged heads; and
 adjusting a position of one of the adjacent vertebral bodies relative to the other of the adjacent vertebral bodies.

15. The method of claim 14, wherein adjusting the position of the one of the adjacent vertebral bodies includes rotating the actuator.

16. The method of claim 14, further comprising activating one or more of the fastener restricting mechanisms to retain the first and second fasteners.

17. The method of claim 14, wherein a portion of the frame member is made of a radiolucent material.

18. The method of claim 14, wherein one or both of a superior surface and an inferior surface of the frame member includes a plurality of projections for gripping an adjacent bony surface.

19. The method of claim 14, further comprising activating a blocking mechanism for retaining a position of the actuator.

20. A method of aligning vertebral bodies comprising the steps of:
 positioning a vertebral implant between a first and second vertebral body, the vertebral implant comprising:
  a frame having a posterior end and an anterior end, the frame includes a central section, a right lateral section, and left lateral section, the central section includes a longitudinal member having a lumen, the longitudinal member extends from the posterior end to the anterior end of the frame;
  a reducing plate configured to be slidably received over the longitudinal member, wherein the reducing plate is configured to be secured to a second vertebral body; and
  an actuator configured to extend through an opening in the reducing plate and into the lumen of the longitudinal member, the actuator configured to move the reducing plate relative to the frame,
  wherein the central section, the right lateral section and the left lateral section are integrally formed,
  wherein the assembly includes a first endplate and a second endplate, the first endplate coupled to the left lateral section of the frame and the second endplate coupled to the right lateral section of the frame, wherein the frame includes an enlarged head portion configured to receive a fastener for securing the assembly to the first vertebral body, wherein the enlarged head portion is further configured to receive a fastener restricting mechanism for limiting longitudinal travel of the fastener, and
  wherein the fastener restricting mechanism includes a screw having a head portion including a cutout therein; and
 actuating the reducing plate to align the first and second vertebral bodies; and
 securing the vertebral implant to the first and second vertebral bodies.

* * * * *